United States Patent
Yoshioka et al.

(10) Patent No.: US 10,285,616 B2
(45) Date of Patent: May 14, 2019

(54) MYOELECTRIC POTENTIAL MEASUREMENT DEVICE AND MYOELECTRIC POTENTIAL MEASUREMENT METHOD

(71) Applicant: Panasonic Intellectual Property Management Co., Ltd., Osaka (JP)

(72) Inventors: Mototaka Yoshioka, Osaka (JP); Jun Ozawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 962 days.

(21) Appl. No.: 14/788,852

(22) Filed: Jul. 1, 2015

(65) Prior Publication Data

US 2016/0007876 A1 Jan. 14, 2016

(30) Foreign Application Priority Data

Jul. 8, 2014 (JP) ................. 2014-140808

(51) Int. Cl.
*A61B 5/00* (2006.01)
*G06F 3/01* (2006.01)
*A61B 5/0492* (2006.01)

(52) U.S. Cl.
CPC ............ *A61B 5/0492* (2013.01); *G06F 3/015* (2013.01); *G06F 3/017* (2013.01); *A61B 5/681* (2013.01);
(Continued)

(58) Field of Classification Search
CPC ....... G06F 3/015; G06F 3/017; A61B 5/0492; A61B 5/681; A61B 5/6824; A61B 2562/043
See application file for complete search history.

(56) References Cited

U.S. PATENT DOCUMENTS 6,244,873 B1 * 6/2001 Hill ..................... G06F 3/015
379/110.01
7,333,090 B2 * 2/2008 Tanaka .................. B25J 9/1656
345/158

(Continued)

FOREIGN PATENT DOCUMENTS

JP 2002-287869 10/2002

*Primary Examiner* — Adam J Eiseman
(74) *Attorney, Agent, or Firm* — McDermott Will & Emery LLP

(57) ABSTRACT

Provided is a myoelectric potential measurement device that recognizes a user arm movement, including a bracelet having a plurality of electrodes, at least one memory, and a processor. The processor: uses the bracelet having the plurality of electrodes, which come into contact with the arm of the user, to measure a myoelectric potential at each of the plurality of electrodes; detects a measurement state when the each myoelectric potential is being measured; specifies at least one preferred electrode, which has a portion of the arm of the user positioned vertically thereunder, from among the plurality of electrodes in accordance with the measurement state, and weights the each myoelectric potential measured by the specified at least one preferred electrode, with respect to the each myoelectric potential measured by electrodes other than the preferred electrode from among the plurality of electrodes; and uses the weighted myoelectric potential to recognize the movement of the user, and outputs a recognition result.

10 Claims, 33 Drawing Sheets

(52) U.S. Cl.
CPC ....... *A61B 5/6824* (2013.01); *A61B 2562/043* (2013.01)

(56) References Cited

U.S. PATENT DOCUMENTS

| | | | | |
|---|---|---|---|---|
| 9,037,530 | B2* | 5/2015 | Tan | A61B 5/0488 706/62 |
| 9,958,949 | B2* | 5/2018 | Morikawa | A61B 5/0488 |
| 2002/0183647 | A1* | 12/2002 | Gozani | A61B 5/0488 600/554 |
| 2009/0327171 | A1* | 12/2009 | Tan | G06F 3/015 706/12 |
| 2015/0182160 | A1* | 7/2015 | Kim | A61B 5/0488 600/301 |

\* cited by examiner

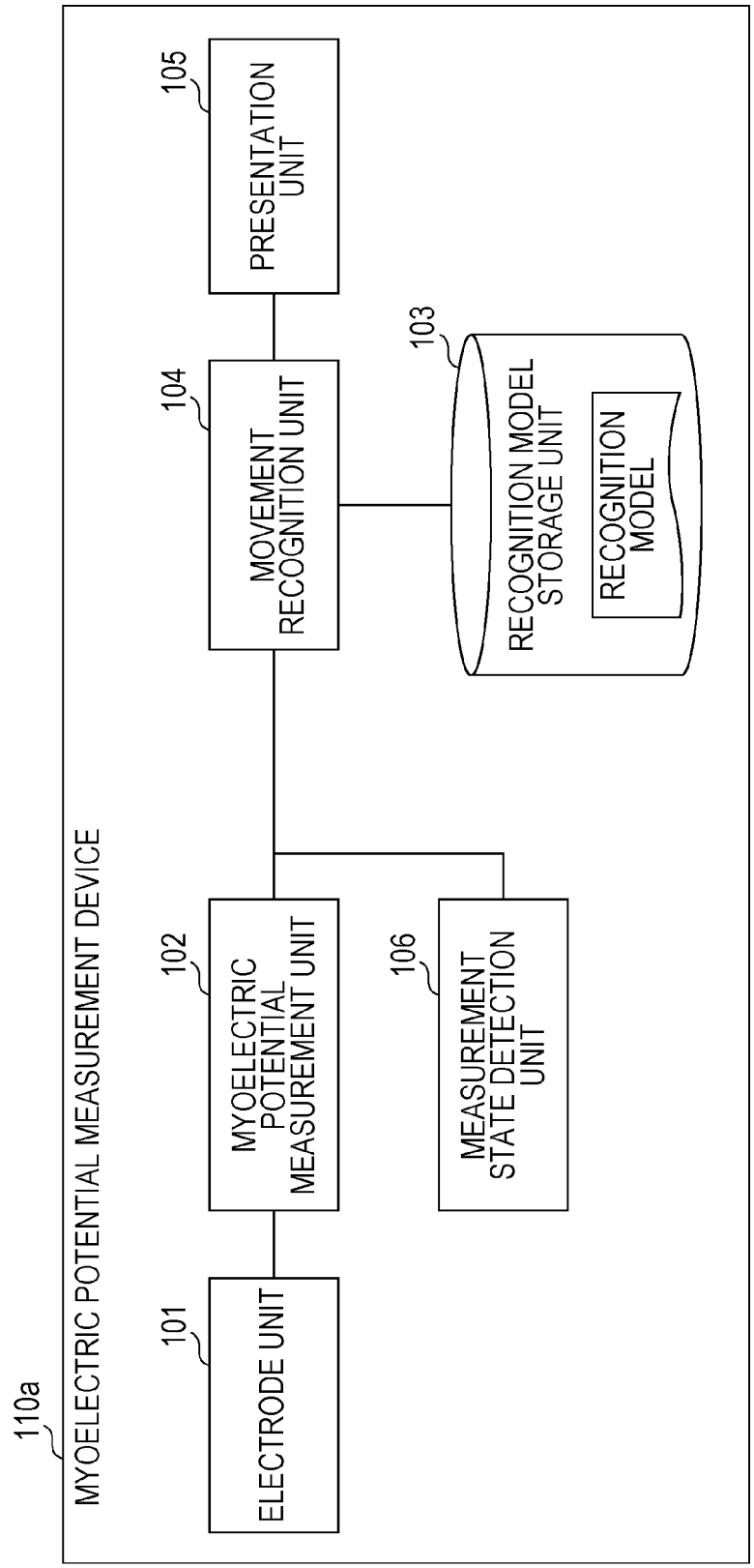

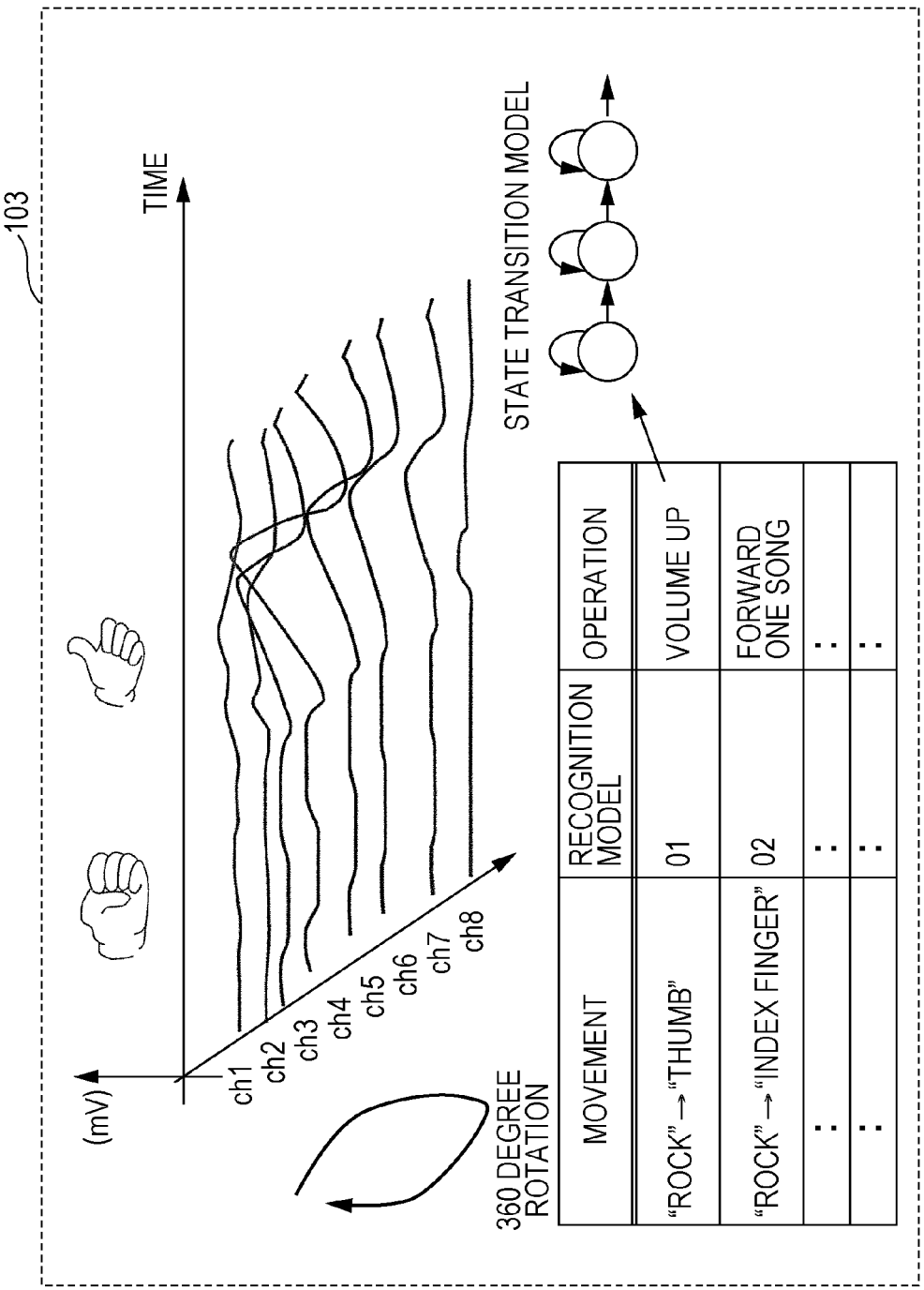

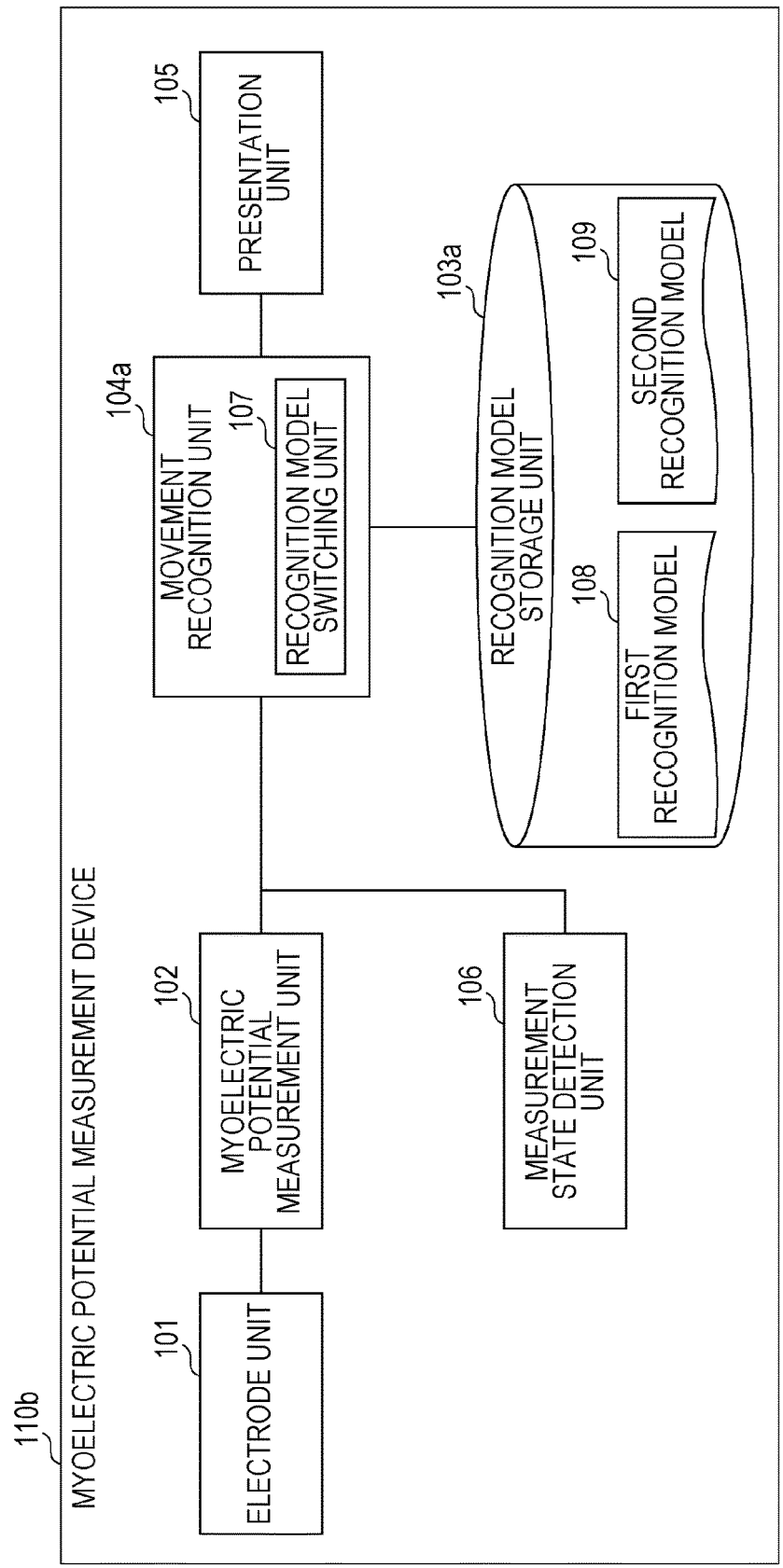

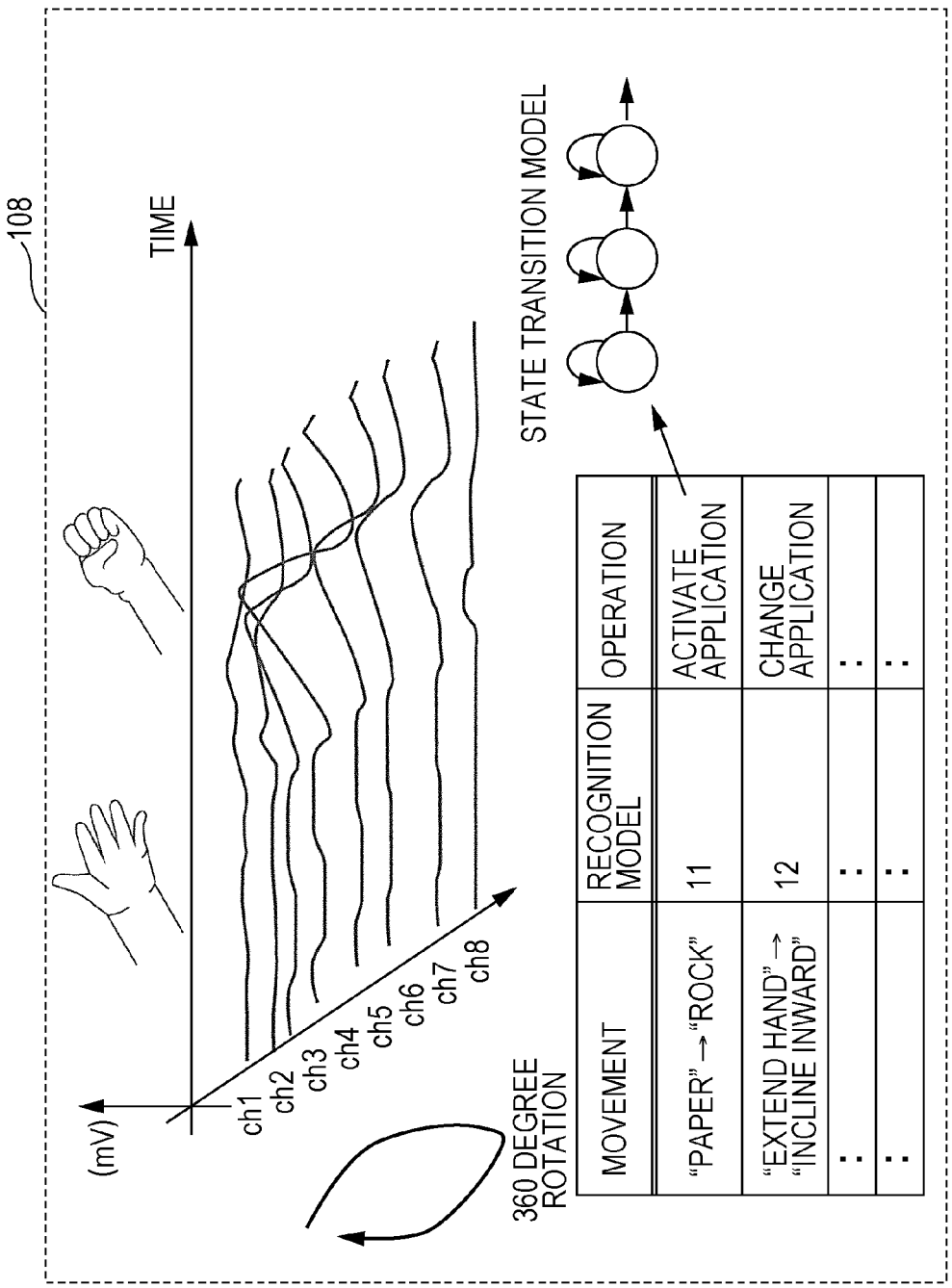

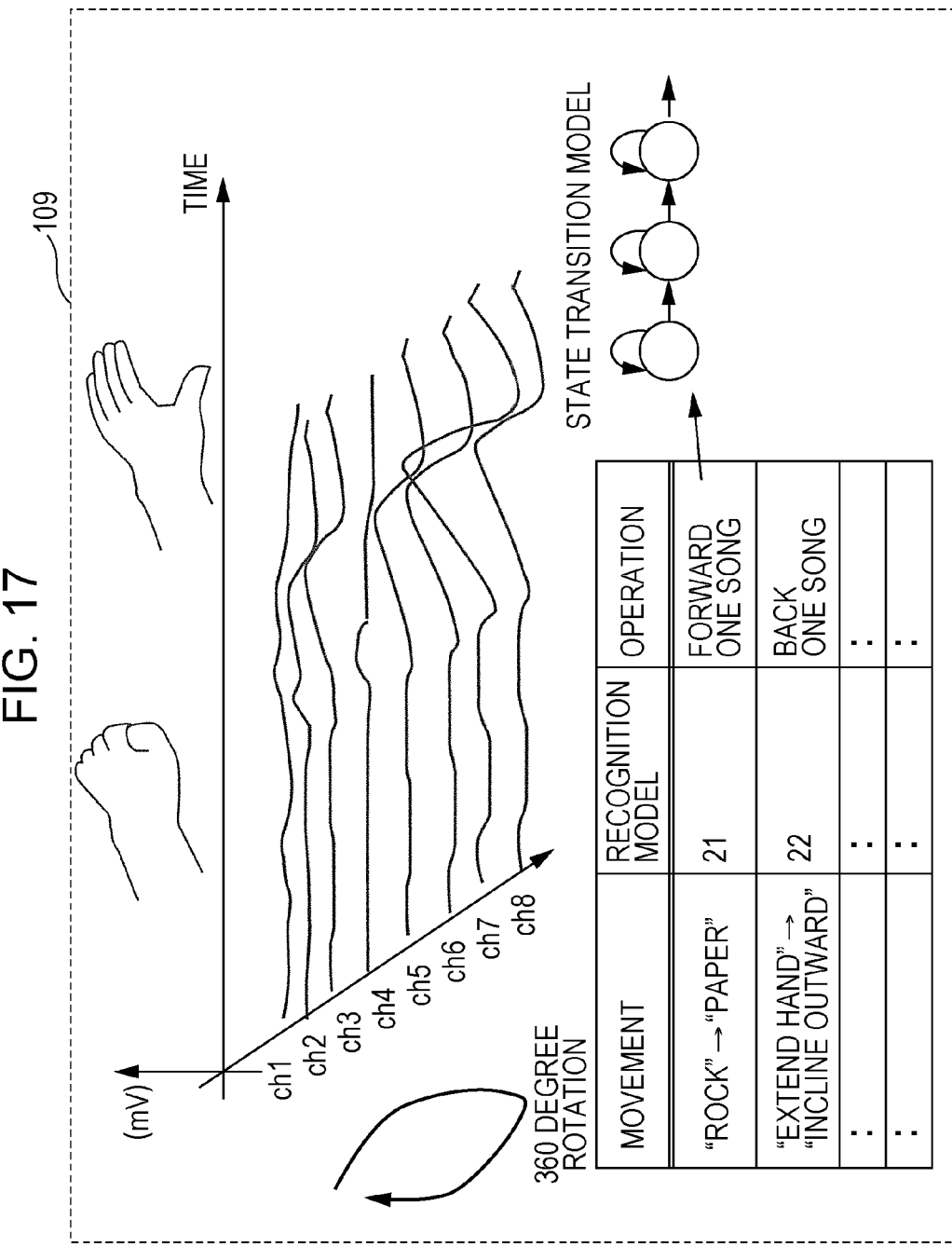

| ACCELERATION IN Z-AXIS DIRECTION | RECOGNITION MODULE |
|---|---|
| Z < 0.4 G | × (WRIST IS LOW) |
| 0.2 G < Z < 0.8 G | ○ (WRIST IS IN FRONT OF CHEST) |
| 0.8 G < Z | × (WRIST IS HIGHER THAN CHEST) |

MYOELECTRIC POTENTIAL MEASUREMENT DEVICE AND MYOELECTRIC POTENTIAL MEASUREMENT METHOD

BACKGROUND

1. Technical Field

The present disclosure relates to a device that measures a myoelectric potential, and particularly relates to a myoelectric potential measurement device provided with an annular electrode unit having a plurality of electrodes that come into contact with an arm of a user.

2. Description of the Related Art

A user interface device in which myoelectric potentials are used is disclosed in Japanese Unexamined Patent Application Publication No. 2002-287869. This user interface device uses information obtained from myoelectric potential sensors to recognize a movement, and operates a device corresponding to the recognized movement. By interpreting the information of a plurality of myoelectric potential sensors as a spatial distribution, the user interface device takes with the rotational displacement of a device attached to a wrist into consideration when recognizing myoelectric potentials.

SUMMARY

However, in the conventional technology disclosed in Japanese Unexamined Patent Application Publication No. 2002-287869, the device is used in a state in which all of a plurality of electrodes are constantly in close contact with the skin of the user, and consideration is not given to the device being used in a state in which any of the electrodes are separate from the skin of the user.

It is necessary to use electrodes that are in contact with the skin of the user in order to acquire a biological signal of the user that includes a myoelectric potential. However, pressure is applied to the skin of the user as a result of the electrodes constantly being in close contact with the skin of the user in the everyday life of the user, and this causes the user to sweat. Thus, there are cases where it is not desirable for all of the electrodes to constantly be in close contact with the skin. For example, when a myoelectric potential measurement device is attached to a wrist like a wristwatch, it is more desirable for there to be a predetermined gap between the myoelectric potential measurement device and the wrist.

However, when there is a predetermined gap between the myoelectric potential measurement device and the wrist, a state occurs where the wrist and some of the electrodes do not come into contact with each other or the connection therebetween is insufficient, and, consequently, there are cases where noise is generated and it is not possible for the recognition of myoelectricity to be carried out in a precise manner in that state.

One non-limiting and exemplary embodiment provides a myoelectric potential measurement device having a plurality of electrodes that come into contact with an arm of a user, the myoelectric potential measurement device and so forth being able to recognize a movement of the arm with a myoelectric potential being appropriately measured even when not all of the plurality of electrodes are in close contact with the arm.

In one general aspect, the techniques disclosed here feature a myoelectric potential measurement device includes a bracelet having a plurality of electrodes, at least one memory, and a processor, wherein the processor performs:

(a) using the bracelet having the plurality of electrodes, which come into contact with the arm of the user, to measure a myoelectric potential at each of the plurality of electrodes;
(b) detecting a measurement state when each myoelectric potential is being measured; (c) specifying at least one preferred electrode, which has a portion of the arm of the user positioned vertically thereunder, from among the plurality of electrodes in accordance with the measurement state, and weighting the myoelectric potential measured by the at least one specified preferred electrode, with respect to the each myoelectric potential measured by electrodes other than the at least one preferred electrode from among the plurality of electrodes; and (d) using the weighted myoelectric potential to recognize the movement of the arm of the user, and outputting a recognition result.

According to the present disclosure, a myoelectric potential measurement device is realized having a plurality of electrodes that come into contact with an arm of a user, the myoelectric potential measurement device and so forth being able to recognize a movement of the arm with a myoelectric potential being appropriately measured even when not all of the plurality of electrodes are in close contact with the arm.

It should be noted that this aspect may be realized by a system, a method, an integrated circuit, or a recording medium such as a computer-readable CD-ROM, and may be realized by an arbitrary combination of a system, a method, an integrated circuit, and a recording medium.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1 is a block diagram depicting the configuration of a myoelectric potential measurement device in Embodiment 1;

FIG. 3 is a drawing depicting a recognition model of a recognition model storage unit of the myoelectric potential measurement device;

FIG. 13 is a block diagram depicting the configuration of a myoelectric potential measurement device in Embodiment 2;

FIG. 16 is a drawing depicting an example of a first recognition model stored in a recognition model storage unit of the myoelectric potential measurement device;

FIG. 17 is a drawing depicting an example of a second recognition model stored in the recognition model storage unit of the myoelectric potential measurement device;

DETAILED DESCRIPTION

Figure 2A:
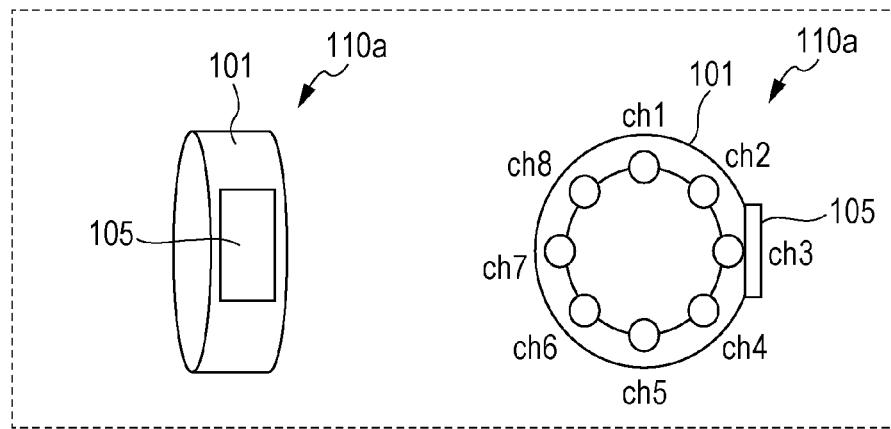
FIG. 2A is an external view of the myoelectric potential measurement device.

A myoelectric potential measurement device includes a bracelet having a plurality of electrodes, at least one memory, and a processor, wherein the processor performs: (a) using the bracelet having the plurality of electrodes, which come into contact with the arm of the user, to measure a myoelectric potential at each of the plurality of electrodes; (b) detecting a measurement state when each myoelectric potential is being measured; (c) specifying at least one preferred electrode, which has a portion of the arm of the user positioned vertically thereunder, from among the plurality of electrodes in accordance with the measurement state, and weighting the myoelectric potential measured by the at least one specified preferred electrode, with respect to the each myoelectric potential measured by electrodes other than the at least one preferred electrode from among the plurality of electrodes; and (d) using the weighted myoelectric potential to recognize the movement of the arm of the user, and outputting a recognition result.

Thus, the movement of the arm is recognized with a myoelectric potential measured by an electrode that is likely to be in close contact with the arm having being prioritized over a myoelectric potential measured by an electrode that is unlikely to be in close contact with the arm. Thus, in the myoelectric potential measurement device having the plurality of electrodes that come into contact with the arm of the user, a movement of the arm is recognized with a myoelectric potential being appropriately measured even when not all of the plurality of electrodes are in close contact with the arm.

Here, a recognition model storage unit that stores recognition models indicating myoelectric potential change patterns obtained by the plurality of electrodes for each of a plurality of types of arm movements may be additionally provided, and the movement recognition unit may recognize a movement of the arm by matching myoelectric potential change patterns measured by the myoelectric potential measurement unit and the change patterns indicated by the recognition models.

Thus, a movement of the arm is recognized with matching being carried out between measured myoelectric potential change patterns and reference myoelectric potential change patterns, and therefore the movement recognition that is carried out has a high degree of precision compared with movement recognition that is based on a momentary myoelectric potential.

Furthermore, the movement recognition unit may carry out the matching with a correction having been carried out to suppress the myoelectric potential measured by the non-preferred electrode to a greater extent than the myoelectric potential measured by the preferred electrode.

Thus, the matching between measured myoelectric potential change patterns and reference myoelectric potential change patterns is carried out with a correction having been carried out to suppress myoelectric potentials measured by electrodes that are unlikely to be in close contact with the arm, thereby enabling highly precise movement recognition.

Furthermore, movements of the hand connected to the arm may be included in the plurality of types of arm movements.

Thus, movements of the hand and a finger are also recognized in addition to movements of the arm.

Furthermore, a presentation unit that presents a recognition result obtained by the movement recognition unit may be additionally provided.

Thus, the user is able to visually be aware of the recognition result due to the recognition result being presented by the presentation unit.

Furthermore, the measurement state detection unit may detect a measurement state by specifying the direction of gravity in the myoelectric potential measurement device.

Thus, a myoelectric potential measurement state may be detected by a sensor such as an acceleration sensor provided in the myoelectric potential measurement device.

Furthermore, the measurement state detection unit may detect a measurement state by specifying the direction of gravity in the presentation unit.

Thus, a myoelectric potential measurement state may be detected by a sensor such as an acceleration sensor provided in the presentation unit.

Furthermore, the recognition model storage unit may store a plurality of different recognition models as the aforementioned recognition models, and the movement recognition unit may include a recognition model switching unit that selects one recognition model from the plurality of recognition models on the basis of the measurement state detected by the measurement state detection unit, and may use the recognition model selected by the recognition model switching unit to recognize a movement of the arm. For example, the plurality of recognition models may include a first recognition model indicating myoelectric potential change patterns for an arm movement with which anterior-side myoelectric potentials are likely to occur, and a second recognition model indicating myoelectric potential change patterns for an arm movement with which posterior-side myoelectric potentials are likely to occur.

Thus, since one recognition model is to be selected from the plurality of recognition models in accordance with the myoelectric potential measurement state, a plurality of recognition models corresponding to arm movements that correspond to myoelectric potential measurement states are stored in advance, thereby enabling movement recognition having even greater precision.

Furthermore, a measurement state storage unit that stores changes that occur over time in the measurement state detected by the measurement state detection unit may be additionally provided, and the movement recognition unit may determine whether or not the wrist of the arm is within a predetermined space of the body of the user on the basis of the changes that occur over time in the measurement state stored in the measurement state storage unit, and may recognize a movement of the arm if it is determined that the wrist is within the predetermined space. For example, the predetermined space may be a space that is set in a position that is higher than the elbow of the arm, and the movement recognition unit may recognize a movement of the arm if the wrist has entered within the predetermined space after having been lowered.

Arm movement recognition is thereby started when the wrist has entered within the predetermined space, and it is therefore possible to avoid movement recognition being started at an unintended timing.

Furthermore, the measurement state detection unit may include an acceleration sensor that detects the direction of gravitational acceleration as the measurement state, and the movement recognition unit may determine whether or not the wrist is within the predetermined space on the basis of changes that occur over time in the direction of the gravitational acceleration stored in the measurement state storage unit.

Thus, the measurement state detection unit may be realized using a widely-used acceleration sensor.

It should be noted that these comprehensive or specific aspects may be realized by using a system, a method, an integrated circuit, a computer program, or a recording medium such as a computer-readable CD-ROM.

Hereinafter, embodiments of the myoelectric potential measurement device, the myoelectric potential measurement method, and the program therefor of the present disclosure will be described with reference to the drawings.

Embodiment 1

First, a myoelectric potential measurement device according to Embodiment 1 of the present disclosure will be described.

FIG. 1 is a block diagram depicting the configuration of a myoelectric potential measurement device 110a in Embodiment 1 of the present disclosure. The myoelectric potential measurement device 110a is a device that measures a myoelectric potential of an arm of a user and recognizes a movement of the arm on the basis of a measurement result thereof, and is provided with an electrode unit 101, a myoelectric potential measurement unit 102, a recognition model storage unit 103, a movement recognition unit 104, a presentation unit 105, and a measurement state detection unit 106. It should be noted that, in the present embodiment, the myoelectric potential measurement device 110a functions as a user interface device (a gesture input device for operating a terminal with arm and hand gestures) for operating a terminal (not depicted).

(Electrode Unit 101)

The electrode unit 101 is an annular structure having a plurality of electrodes that come into contact with the arm of the user. An annular structure means a bracelet. It should be noted that an arm means the portion from the shoulder to the hand and includes not only the forearm (lower arm) but also the upper arm and the wrist, and typically means the forearm (lower arm) including the wrist. The electrode unit 101 is formed as a ring-shaped belt-like structure that is attached to the arm, and has a front surface and a rear surface. It should be noted that the surface that comes into contact with the arm when the user has attached the electrode unit 101 is referred to as the rear surface, and the opposite surface to the rear surface is referred to as the front surface. The electrode unit 101 has a plurality of electrodes arranged on the rear surface of the electrode unit 101.

The plurality of electrodes of the electrode unit 101 are formed from silver chloride or the like, for example. It should be noted that the electrode unit 101 may have an amplifier circuit that is connected to each of the plurality of electrodes, and may have active-type electrodes that suppress noise generated by a lead wire or the like that transmits signals from the electrodes. It thereby becomes possible to measure a myoelectric potential by contact being made with the skin even when there is no paste.

Figure 2B:
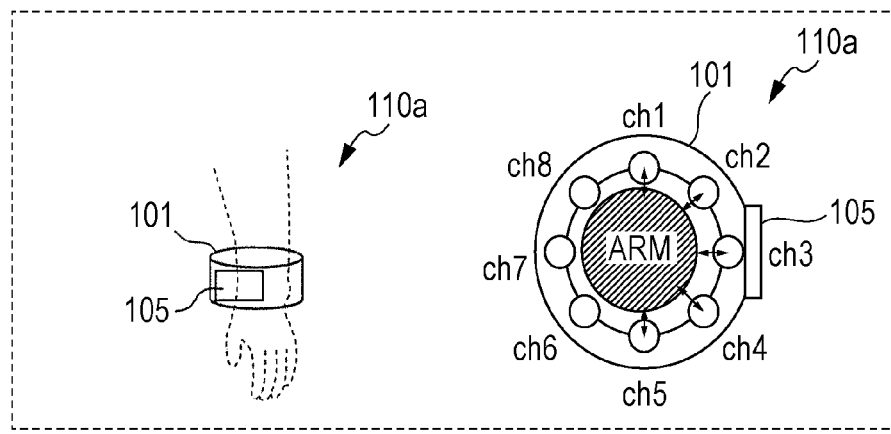
FIG. 2B is an external view of the myoelectric potential measurement device.
Figure 2C:
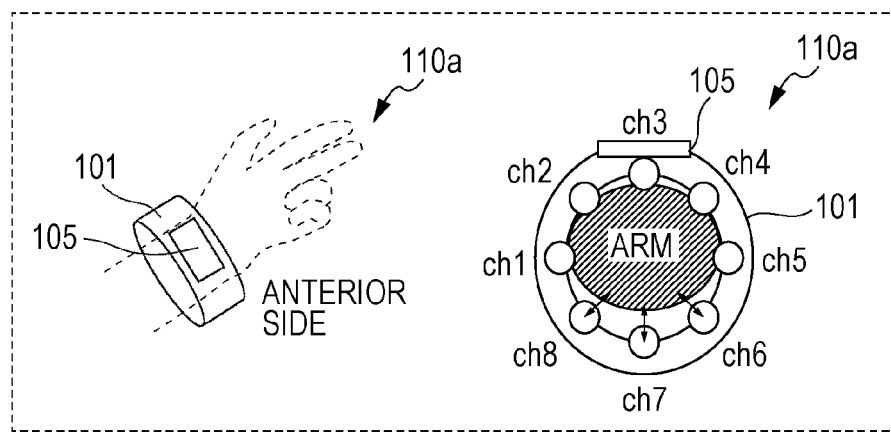
FIG. 2C is an external view of the myoelectric potential measurement device.

FIGS. 2A to 2C are drawings depicting examples of an external view of the myoelectric potential measurement device 110a according to the present embodiment. As depicted in FIG. 2A, the myoelectric potential measurement device 110a in the present embodiment has the annular electrode unit 101 so as to be able to attach to an arm. Furthermore, by having the plurality of electrodes (eight electrodes ch1 to ch8 in the present example) arranged on the rear surface (inside surface) of the annular electrode unit 101 as depicted in FIG. 2A, and attaching the myoelectric potential measurement device 110a (the electrode unit 101, strictly speaking) to the arm, myoelectric potentials that accompany a gesture of the hand and so forth are measured and movements of the arm including the hand are recognized from the measured myoelectric potentials, and it thereby becomes possible to carry out operations (gesture inputs) with respect to the terminal.

In an everyday environment, pressure is applied to the skin and sweating and so forth occurs when an electrode is constantly in close contact with the skin, and there are cases where it is not desirable for all of the electrodes to always be in close contact with the skin. In contrast, similar to a wristwatch or a bracelet, the myoelectric potential measurement device 110a presented in the present embodiment has a predetermined gap between the electrode unit 101 and the arm when attached.

FIG. 2B is a drawing depicting the attachment state of the myoelectric potential measurement device 110a when the arm has been lowered. Since the peripheral length (peripheral length of the inner circumference) of the electrode unit 101 is quite large with respect to the peripheral length of the arm, it is understood that there is a gap between the arm and the electrode unit 101 and there is a section where electrodes do not make contact.

FIG. 2C is a drawing depicting a state in which the user has raised his/her arm and directed his/her palm in the direction of his/her face, and the user is operating (inputting a gesture to) the terminal while looking at the presentation unit 105 in order to operate the terminal by using the myoelectric potential measurement device 110a as a user interface device. A situation occurs in which there is a gap between the arm and the electrode unit 101, the electrode unit 101 lowers vertically downward with the arm as a supporting point due to the effect of gravity, and the electrodes ch6 to ch8 at the lower side either do not come into contact with the arm or the contact with the arm is insufficient.

When there is a predetermined gap between the arm and the electrode unit 101 in this way, a state occurs in which some of the electrodes from among the plurality of electrodes either do not come into contact with the arm or the contact is insufficient, and noise is therefore generated in the myoelectric potentials measured by such electrodes, and there are cases where arm movement recognition cannot be carried out in a precise manner.

Therefore, in the present embodiment, myoelectric potentials measured by the plurality of electrodes are corrected depending on the measurement state of the myoelectric potentials and arm movement recognition is carried out based on the corrected myoelectric potentials. As a result, arm movement recognition is appropriately carried out even when not all of the plurality of electrodes are in close contact with the arm.

(Recognition Model Storage Unit 103)

The recognition model storage unit 103 is a storage unit that stores recognition models indicating change patterns (reference change patterns) for myoelectric potentials obtained for the plurality of electrodes of the electrode unit 101, for each of a plurality of types of arm movements. FIG. 3 depicts the way in which data that indicates change patterns (reference change patterns) for myoelectric potentials obtained by the electrodes ch1 to ch8 in a movement from "a clenched first to a raised thumb" as an example of a movement is stored as one model (recognition model "01"). Furthermore, an "increase volume (volume up)" instruction is stored as a terminal operation (operation as a user interface device) that corresponds to this movement. The recognition models representing change patterns are time-sequential statistical models such as a hidden Markov model, in which, more specifically, the root mean squares (RMS) of myoelectric potentials that change due to an arm movement and state changes that occur over time are stored as state output values and state transition probabilities.

(Myoelectric Potential Measurement Unit 102)

The myoelectric potential measurement unit 102 is a measurement unit that measures myoelectric potentials at each of the plurality of electrodes and, in the present embodiment, uses the plurality of electrodes ch1 to ch8 to measure myoelectric potentials at a plurality of locations in the circumferential direction of the arm. For example, the myoelectric potential measurement unit 102 measures the difference in potential between each of the electrodes ch1 to ch8 and a reference electrode (not depicted).

Figure 4:
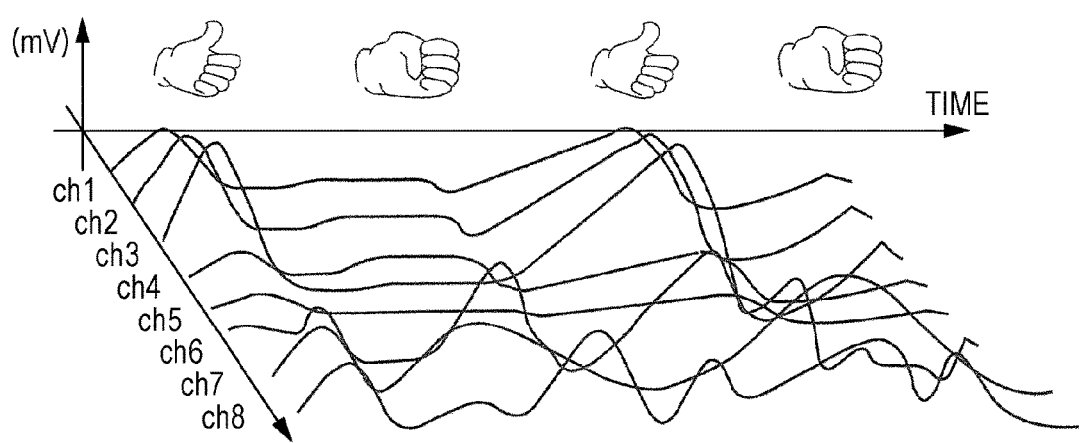
FIG. 4 is a drawing depicting myoelectric potentials measured by a myoelectric potential measurement unit of the myoelectric potential measurement device.

FIG. 4 is a drawing depicting an example of myoelectric potentials (changes that occur over time in myoelectric potentials) acquired by each electrode ch1 to ch8. For example, when using the myoelectric potential measurement device 110a to operate (input gestures to) a terminal as depicted in FIG. 2C, the user raises his/her arm upward, directs his/her hand toward the inside, and repeats the movement from a clenched first to a raised thumb while looking at the presentation unit 105. With this kind of movement, it is understood that myoelectric potentials are generated in each electrode ch1 to ch8, and the generated myoelectric potentials are detected by the myoelectric potential measurement unit 102. Furthermore, in a state such as this, it is understood that the myoelectric potential measurement device 110a lowers down (vertically downward) due to gravity and the contact between with the electrodes ch6 to ch8 and the arm is insufficient as depicted in FIG. 2C, and noise is consequently generated in the electrodes ch6 to ch8 (amplitude becomes extremely high).

(Measurement State Detection Unit 106)

The measurement state detection unit 106 is a processing unit that detects the state (measurement state) in which myoelectric potentials are measured by the myoelectric potential measurement unit 102. In the present embodiment, the measurement state detection unit 106 is constituted by an acceleration sensor, for example, and detects the myoelectric potential measurement state by detecting the angle or direction of the gravitational direction in the myoelectric potential measurement device 110a attached to the arm, on the basis of the gravitational direction measured by the acceleration sensor. In other words, in the present embodiment, the measurement state detection unit 106 detects the measurement state by specifying the direction of gravity in the myoelectric potential measurement device 110a. It should be noted that the measurement state detection unit 106 may detect the measurement state by specifying the direction of gravity in the presentation unit 105 in addition to or instead of the direction of gravity in the myoelectric potential measurement device 110a.

Figure 5A:
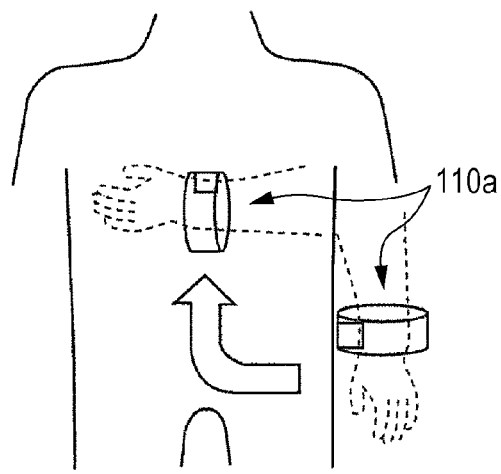
FIG. 5A is a drawing illustrating an example of the detection of a measurement state by the measurement state detection unit of the myoelectric potential measurement device.
Figure 5B:
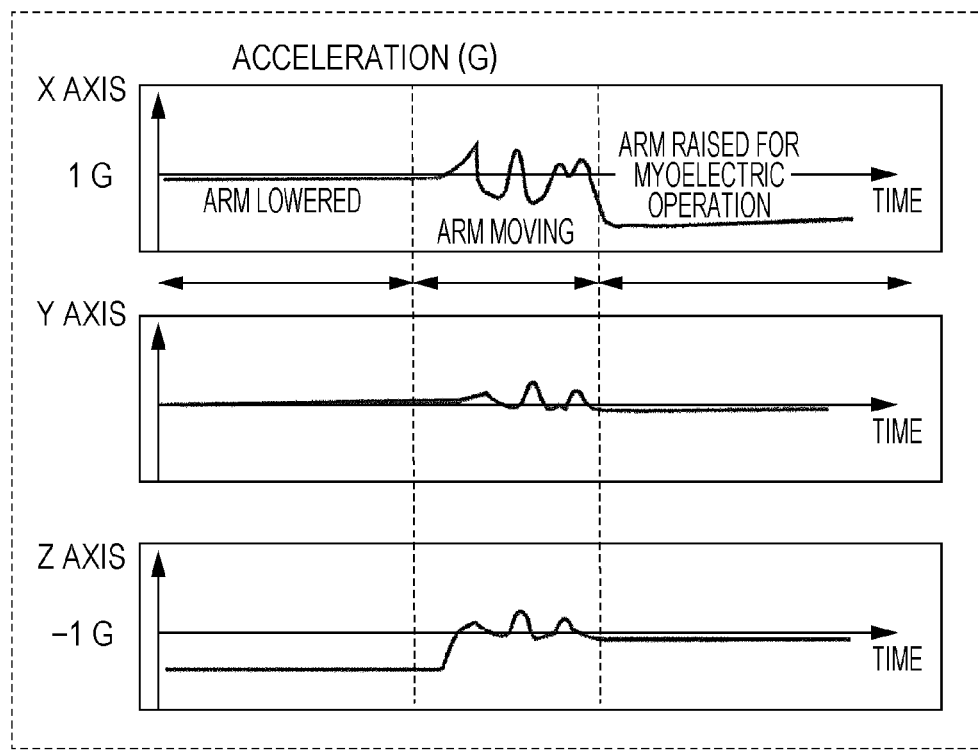
FIG. 5B is a drawing depicting an example of the measurement of acceleration by the measurement state detection unit of the myoelectric potential measurement device.

FIGS. 5A to 5E are drawings illustrating an example of the detection of the measurement state by the measurement state detection unit 106 (here, an example of the detection of the orientation of the myoelectric potential measurement device 110a attached to the arm). FIGS. 5A to 5E respectively depict the orientation of the myoelectric potential measurement device 110a, the direction of gravitational acceleration detected by the measurement state detection unit 106, the orientation of the myoelectric potential measurement device 110a prior to the arm being moved as depicted in FIG. 5A, and the orientation of the myoelectric potential measurement device 110a after the arm has been moved. It should be noted that the "orientation of the myoelectric potential measurement device 110a" means the orientation of the myoelectric potential measurement device 110a with respect to gravity, and also means the direction of gravity (gravitational direction) in the myoelectric potential measurement device 110a.

Figure 5C:
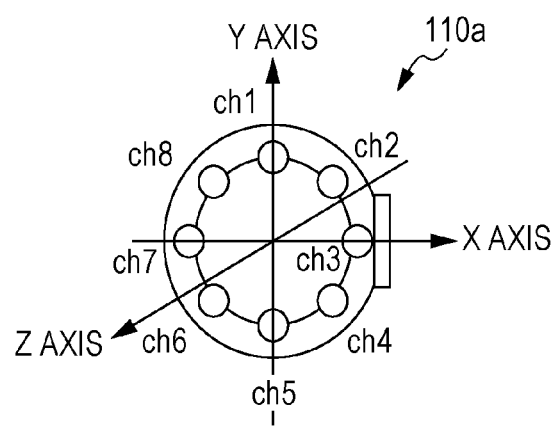
FIG. 5C is a drawing illustrating an example of the detection of a measurement state by the measurement state detection unit of the myoelectric potential measurement device.

Furthermore, regarding coordinate axes in the myoelectric potential measurement device 110a, as depicted in FIG. 5C, the direction from the position of the electrode ch7 toward the position of the electrode ch3 (the direction in which the presentation unit 105 is installed) is taken as the X axis, the direction from the position of the electrode ch5 toward the position of the electrode ch1 is taken as the Y axis, and the direction from the rear of the drawing (namely, the tip of the hand) toward the front of the drawing (namely, the arm) in FIG. 5C is taken as the Z axis, FIG. 5C being a drawing in which the myoelectric potential measurement device 110a is seen from the hand. The measurement state detection unit 106 detects the direction of gravity in the myoelectric potential measurement device 110a, namely, gravitational acceleration in the X axis, Y axis, and Z axis depicted in FIG. 5C, as the state of a measurement obtained by the myoelectric potential measurement unit 102.

Figure 5D:
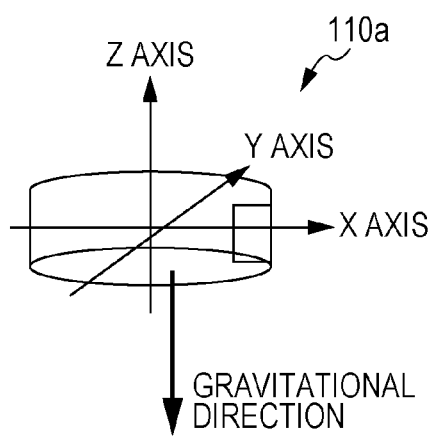
FIG. 5D is a drawing illustrating an example of the detection of a measurement state by the measurement state detection unit of the myoelectric potential measurement device.

Here, it is assumed that the user has attached the myoelectric potential measurement device 110a to the left wrist and the hand has been lowered as depicted in FIG. 5A. In this state, the myoelectric potential measurement device 110a is oriented as depicted in FIG. 5D, gravity acts in the minus direction of the Z axis as indicated by "arm lowered" in the time axis of FIG. 5B, and an acceleration of −1 G is generated in the Z axis as the value of the acceleration sensor of the measurement state detection unit 106.

Figure 5E:
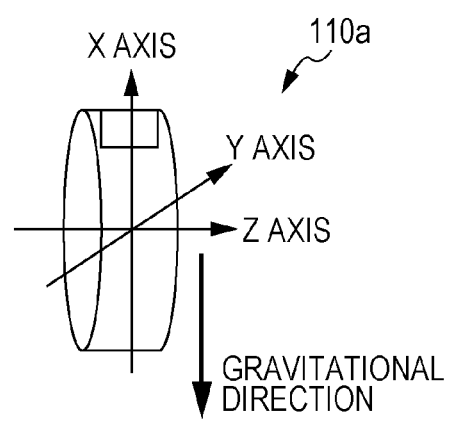
FIG. 5E is a drawing illustrating an example of the detection of a measurement state by the measurement state detection unit of the myoelectric potential measurement device.

Next, as depicted in FIG. 5A, the user raises his/her arm in order to carry out a myoelectric operation (using the myoelectric potential measurement device as a user interface device to operate an operation-target terminal), and it is assumed that the myoelectric potential measurement device 110a enters a state in which the presentation unit 105 is oriented upward. In this state, the myoelectric potential measurement device 110a is oriented as depicted in FIG. 5E, and it is understood that the gravitational direction changes from the minus direction of the Z axis to the minus direction of the X axis as indicated by "arm is moving" and "arm is raised" in the time axis of FIG. 5B, and an acceleration of −1 G is generated in the X-axis direction as the value of the acceleration sensor of the measurement state detection unit 106.

The measurement state detection unit 106 detects the direction of gravity in the myoelectric potential measurement device 110a on the basis of acceleration information regarding the gravity applied in each axis, as a myoelectric potential measurement state. In the case of the present example, the presentation unit 105 is oriented upward and gravity is acting in the minus direction of the X axis. In the present embodiment, the measurement state detection unit 106 detects the direction of gravity in the myoelectric potential measurement device 110a as a myoelectric potential measurement state in this way.

It should be noted that, in the present embodiment, a description has been given in which a measurement state is detected by the measurement state detection unit 106 using only an acceleration sensor. With this approach, the myoelectric potential measurement device 110a has fewer constituent components, the size of the sensor is reduced, and processing is facilitated, which also leads to electric power being conserved. However, the acceleration value may be additionally integrated and so forth, and the position or the orientation of the arm may also be detected. Furthermore, it is also possible for the measurement state detection unit 106 to be made up of an acceleration sensor and a gyroscope for information such as an angular velocity to be used and for a detailed position and angle to be calculated. In addition, an altimeter or the like may be used as the measurement state detection unit 106. Thus, it becomes possible to measure height when the arm is raised.

(Movement Recognition Unit 104)

The movement recognition unit 104 is a processing unit that recognizes a movement of the arm on the basis of myoelectric potentials measured by the myoelectric potential measurement unit 102 and outputs a recognition result. In the present embodiment, the movement recognition unit 104 recognizes a movement of the arm by matching myoelectric potential change patterns measured by the myoelectric potential measurement unit 102 and myoelectric potential change patterns indicated by recognition models stored in the recognition model storage unit 103.

At such time, the movement recognition unit 104 specifies preferred electrodes, which are electrodes having a portion of the arm positioned vertically thereunder, from among the plurality of electrodes on the basis of a myoelectric potential measurement state detected by the measurement state detection unit 106, and recognizes a movement of the arm with the myoelectric potentials measured by the specified preferred electrodes having been prioritized over the myoelectric potentials measured by non-preferred electrodes, which are the electrodes other than the preferred electrodes.

Specifically, the movement recognition unit 104 uses myoelectric potentials obtained by using weightings that are described hereinafter to suppress myoelectric potentials measured by the non-preferred electrodes to a greater extent than the myoelectric potentials measured by the preferred electrodes, to carry out matching between measured myoelectric potential change patterns and recognition models. In other words, the movement recognition unit 104 carries out arm movement recognition with matching being carried out between myoelectric potentials measured by the myoelectric potential measurement unit 102 and movement models stored in the recognition model storage unit 103.

In addition, the movement recognition unit 104 takes the state of the arm measured by the measurement state detection unit 106, in other words, in the present embodiment, the situation regarding contact between the electrode unit 101 and the arm, into consideration when recognizing a movement of the arm. As depicted in FIGS. 4 and 5A to 5E, the contact state of the sensor changes according to the state of the arm (namely, the gravitational direction in the myoelectric potential measurement device 110a), and there are cases where it becomes likely for noise to occur and recognition precision to decline when contact is insufficient or there is separation. Thus, in the present embodiment, noise is suppressed by applying a weighting to the myoelectric potential measured by each electrode, in accordance with the measurement state (here, the gravitational direction in the myoelectric potential measurement device 110a) of the myoelectric potential, and changing the weighting.

Specifically, the myoelectric potentials measured by the specified preferred electrodes are weighted with respect to the myoelectric potentials measured by electrodes other than the preferred electrodes from among the plurality of electrodes, and weighted myoelectric potentials are obtained. Examples of weighted myoelectric potentials include: (a) the myoelectric potentials of only the preferred electrodes; (b) potentials obtained by multiplication of a coefficient equal to or greater than 1 and the myoelectric potentials measured by the preferred electrodes, the myoelectric potentials measured by the electrodes other than the preferred electrodes; (c) the myoelectric potentials measured by the preferred electrodes, and potentials obtained by multiplication of a coefficient equal to or less than 1 and the myoelectric potentials measured by the electrodes other than the preferred electrodes. A weighting example is given below.

For example, a weighting $w_n$ that is dependent upon the orientation of the myoelectric potential measurement device 110a is applied to each electrode $ch_n$ (n=1 to 8). The weighting $w_n$ is a value given by Expression 1 below, in which a unit vector of the gravitational direction is g, a unit vector oriented toward the position of the electrode $ch_n$ from the center of the annular electrode unit 101 is $c_n$ (the center point in the case where the electrode unit 101 is considered to be a circle, for example), and the inner product of these is taken.

$$w_n = \begin{cases} 1 & \text{if } 0 \leq -c_n \cdot g \\ 0 & \text{if } 0 > -c_n \cdot g \end{cases} \quad \text{(Expression 1)}$$

In other words, by taking the inner product of a unit vector in the gravitational direction and a unit vector oriented toward the position of each electrode from the center of the electrode unit 101, the obtained weighting $w_n$ is a coefficient that works in a suppression direction to a greater extent the more the electrode that measures a myoelectric potential is positioned in the gravitational direction. Furthermore, in the present embodiment, binary control is performed with the weighting $w_n$ being 1 when the inner product is 0 or more, in other words, with respect to an electrode positioned above a horizontal line passing through the center of the electrode unit 101 (namely, a preferred electrode), and the weighting $w_n$ being 0 when the inner product is less than 0, in other words, with respect to an electrode positioned below the horizontal line passing through the center of the electrode unit 101 (namely, a non-preferred electrode). This is because, when attached to an arm like a wristwatch, the myoelectric potential measurement device 110a has an annular shape and is pulled downward by gravity, and therefore there are cases where the electrodes positioned above the horizontal line passing through the center of the electrode unit 101 come into contact with the arm and the electrodes positioned below the horizontal line passing through the center of the electrode unit 101 make insufficient contact.

By using weightings such as these, the movement recognition unit 104 specifies, from among the plurality of electrodes, electrodes positioned above the horizontal line passing through the center of the electrode unit 101, or to rephrase, electrodes having a portion of the arm positioned vertically thereunder, as preferred electrodes, specifies electrodes positioned below the horizontal line passing through the center of the electrode unit 101, or to rephrase, electrodes other than the preferred electrodes, as non-preferred electrodes, and recognizes a movement of the arm with the myoelectric potentials measured by the preferred electrodes having been prioritized over the myoelectric potentials measured by the non-preferred electrodes.

It should be noted that the movement recognition unit 104 is realized by a nonvolatile memory having a program stored thereon, a CPU such as a processor that executes that program, a nonvolatile memory that is a temporary storage region, and an input/output port for controlling other constituent elements.

Figure 6A:
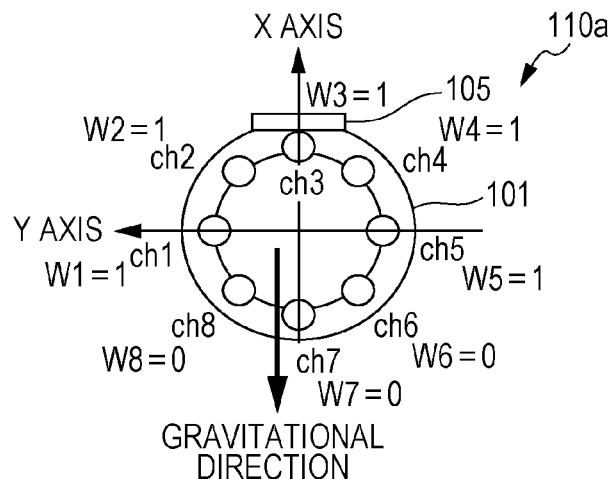
FIG. 6A is a drawing depicting specific examples of weightings applied by a movement recognition unit of the same myoelectric potential measurement device.
Figure 6B:
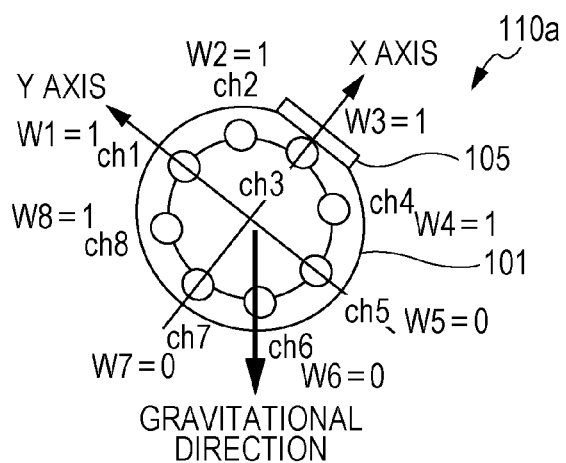
FIG. 6B is a drawing depicting specific examples of weightings applied by the movement recognition unit of the same myoelectric potential measurement device.
Figure 6C:
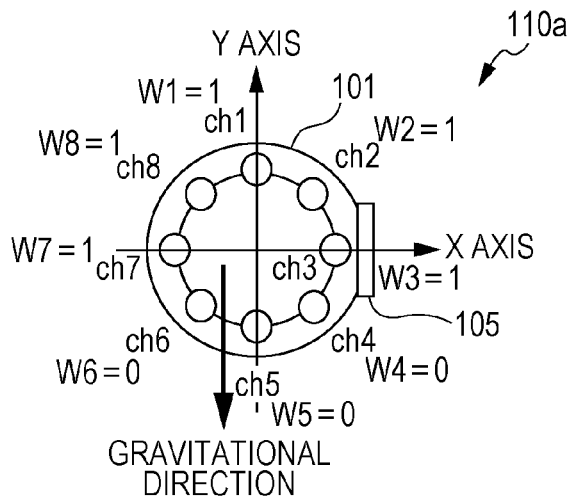
FIG. 6C is a drawing depicting specific examples of weightings applied by the movement recognition unit of the same myoelectric potential measurement device.

FIGS. 6A to 6C are drawings depicting specific examples of weightings applied by the movement recognition unit 104. For example, when the presentation unit 105 is oriented upward as depicted in FIG. 6A and, as a result, the electrode ch3 is oriented in the opposite direction to gravity and the electrode ch7 is oriented in the gravitational direction, according to the aforementioned Expression 1, a weighting of w=1 is applied to the electrodes ch1 to ch5 (specified as preferred electrodes) and a weighting of w=0 is applied to the electrodes ch6 to ch8 (specified as non-preferred electrodes).

When the presentation unit 105 is oriented upward and inclined to some extent (inclined at an angle of 45 degrees, for example) as depicted in FIG. 6B, the presentation unit 105 is positioned at an angle at which the electrode ch2 is oriented in the opposite direction to gravity and the electrode ch6 is oriented in the gravitational direction. In this case, according to the aforementioned Expression 1, a weighting of w=1 is applied to the electrodes ch1 to ch4 and the electrode ch8 (specified as preferred electrodes) and a weighting of w=0 is applied to the electrodes ch5 to ch7 (specified as non-preferred electrodes).

When the presentation unit 105 is oriented directly to the side as depicted in FIG. 6C, the presentation unit 105 is positioned at an angle at which the electrode ch1 is oriented in the opposite direction to gravity and the electrode ch5 is oriented in the gravitational direction. In this case, according to the aforementioned Expression 1, a weighting of w=1 is applied to the electrodes ch7 and ch8 and the electrodes ch1 to ch3 (specified as preferred electrodes) and a weighting of w=0 is applied to the electrodes ch4 to ch6 (specified as non-preferred electrodes). In this way, the movement recognition unit 104 controls the changing connection conditions of the electrodes ch1 to ch8 with weightings in accordance with the myoelectric potential measurement state, namely, the gravitational direction in the myoelectric potential measurement device 110a attached to the arm.

Figure 7:
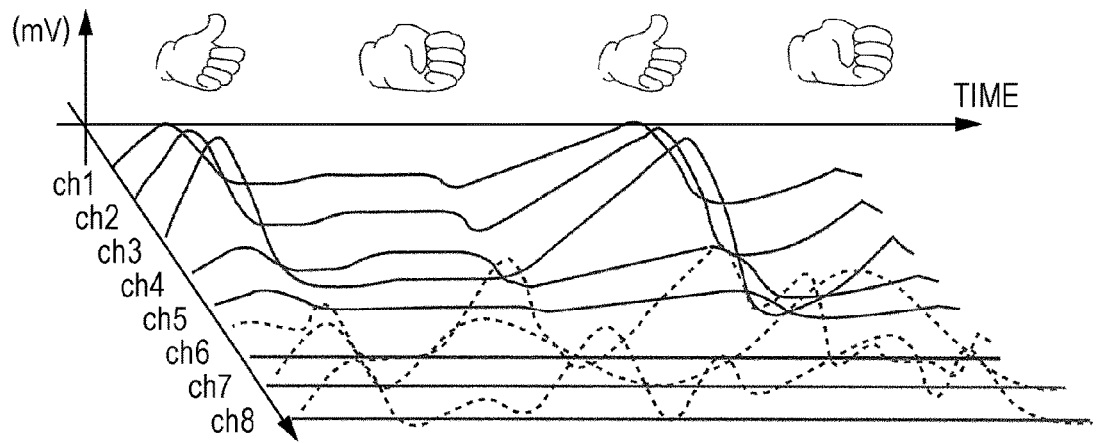
FIG. 7 is a drawing depicting an example of change patterns after multiplication by weightings has been carried out with respect to myoelectric potential change patterns measured by the myoelectric potential measurement device.
Figure 8:
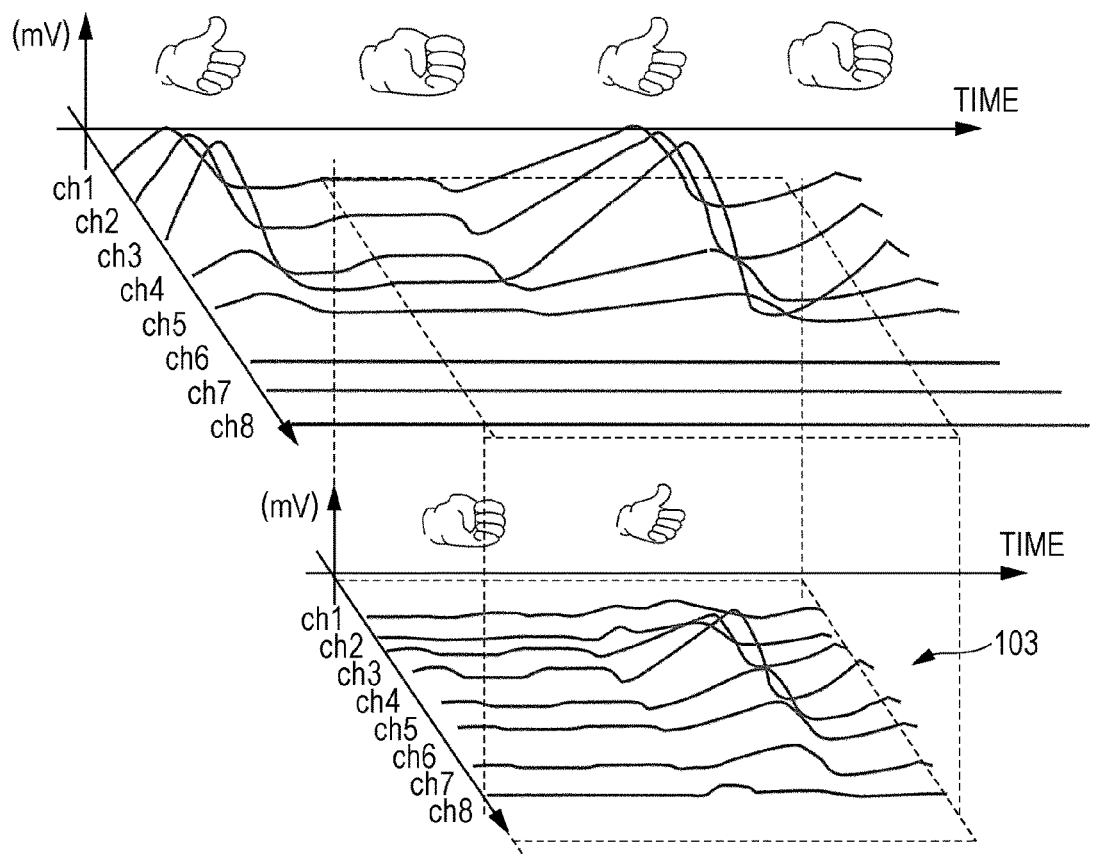
FIG. 8 is a drawing illustrating matching between myoelectric potential change patterns after a correction to suppress noise has been carried out by the myoelectric potential measurement device, and myoelectric potential change patterns indicated by a recognition model.

An operation in which weightings implemented by the movement recognition unit 104 is used will be described using FIGS. 7 and 8. FIG. 7 is a drawing depicting change patterns after multiplication by weightings applied as described above has been carried out with respect to the measured myoelectric potential change patterns depicted in FIG. 4. In FIG. 4, noise is generated in the myoelectric potentials of the electrodes ch6 to ch8 (non-preferred electrodes), whereas, in FIG. 7, it can be seen that the noise has been suppressed with those myoelectric potentials having been multiplied by weightings of w=0. FIG. 8 is a drawing illustrating matching between myoelectric potential change patterns of each electrode ch1 to ch8 after a correction to suppress noise has been carried out in the aforementioned manner (upper section of the drawing) and myoelectric potential change patterns indicated by a recognition model stored in the recognition model storage unit 103 (lower section of the drawing).

The movement recognition unit 104 carries out matching between the myoelectric potential change pattern of each electrode ch1 to ch8 after multiplication with the weightings and the myoelectric potential change patterns indicated by the recognition model, and carries out arm movement recognition. In this way, once a correction to suppress the myoelectric potentials measured by the non-preferred electrodes to a greater extent than the myoelectric potentials measured by the preferred electrodes has been carried out, the movement recognition unit 104 carries out matching between the measured myoelectric potential change patterns and the change patterns indicated by the recognition model and recognizes a movement of the arm.

It should be noted that, various methods such as dynamic programming (DP) are known in relation to the matching of a time-sequential statistical model such as a hidden Markov model with multivariate input as in the present example, and these methods may be used to carry out matching also in the present embodiment. In the example depicted in FIG. 8, a movement from a clenched first shape to a raised thumb is recognized as the corresponding movement.

(Presentation Unit 105)

The presentation unit 105 is a processing unit that displays a recognition result of the movement recognition unit 104, and, for example, has a display screen such as an LCD and acts as a user interface for displaying a recognized movement on that display screen or carrying out some kind of input with respect to the myoelectric potential measurement device 110a and so forth. Presentation unit is expressed with display unit.

Figure 9:
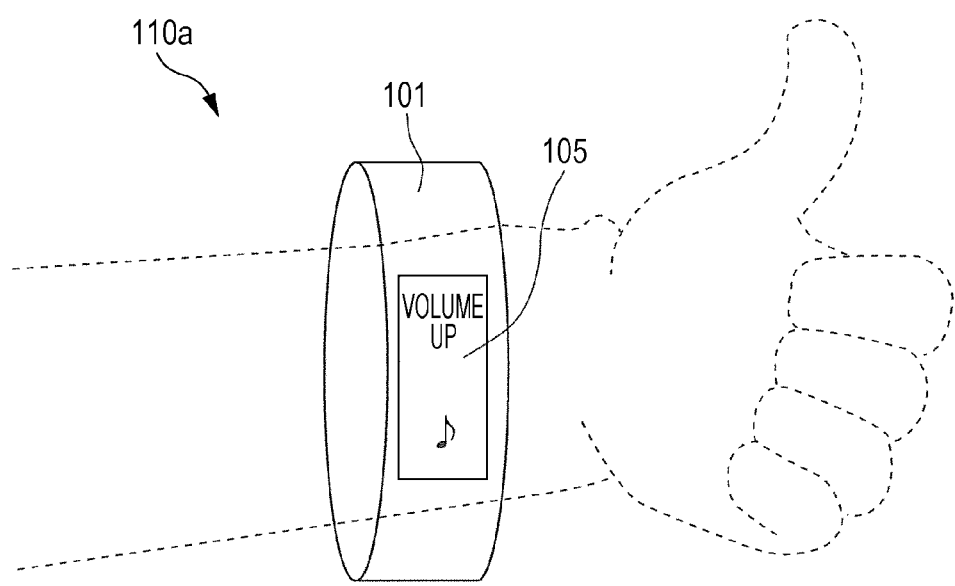
FIG. 9 is a drawing depicting an example presented by a presentation unit of the myoelectric potential measurement device.

FIG. 9 is a drawing depicting an example of the presentation unit 105. Here, for example, the movement of raising a thumb is recognized by the movement recognition unit 104, and information such as "increase volume" is presented as a terminal operation that corresponds to this movement.

In the present embodiment, myoelectric potentials are corrected with a weighting of w=1 being applied to electrodes positioned above the horizontal line passing through the center of the electrode unit 101 and a weighting of w=0 being applied to electrodes positioned below the horizontal line passing through the center of the electrode unit 101; however, it should be noted that the present disclosure is not limited thereto.

There are also cases where the degree of contact is dependent upon the shape of the myoelectric potential measurement device or the material of the annular electrode unit 101. For example, when the gap between the annular electrode unit 101 and the arm is relatively small, there are cases where the electrodes make sufficient contact with the arm even when below the aforementioned horizontal line, and where only the electrodes positioned in the gravitational direction (vertically directly below, or in other words, in the direction directly below and in the vicinity thereof) make insufficient contact. In such cases, adjustment is possible by the inner product not being less than 0 and in addition performing control with a smaller value (a negative value) as a threshold value (in other words, weightings that reflect this kind of contact state can be determined by comparing the smaller value and the inner product and then determining weightings).

Conversely, when the material is hard and the size of the annular shape of the electrode unit 101 is large with respect to the arm, there are cases where electrodes close to the horizontal line have insufficient contact with the arm, even with electrodes positioned above the horizontal line passing through the center of the electrode unit 101. It is possible to handle such cases (in other words, weightings that reflect this kind of contact state can be determined) by altering the threshold value by, for example, setting the threshold value compared with the inner product to be 0.5 or greater (in other words, 60 degrees or less).

Furthermore, rather than separating the weightings into the binary values of 0 and 1 according to the magnitude relationship between the inner product and the threshold value as in the aforementioned Expression 1, a value that progressively changes according to the gravitational direction in the myoelectric potential measurement device 110a may be determined as a weighting. For example, the value of the inner product itself may be used and the weighting $w_n$ may be determined according to the following Expression 2.

$$w_n = (1 - c_n \cdot g)/2 \quad \text{(Expression 2)}$$

By determining the weightings according to this Expression 2, the weighting for the electrode positioned at the opposite side to gravity becomes the largest value (1) and, conversely, the weighting for the electrode positioned in the same direction as gravity becomes the smallest value (0), and, therebetween, values (coefficients that work in the direction in which myoelectric potentials are to be suppressed) become progressively smaller the closer the position of an electrode is to the gravitational direction. In this way, the degree to which the myoelectric potentials measured by the preferred electrodes are prioritized over the myoelectric potentials measured by non-preferred electrodes may be a progressive value for which the degree of contact is taken into consideration.

Next, the flow of an operation (myoelectric potential measurement method) of the myoelectric potential measurement device 110a according to the present embodiment mentioned above is described using FIGS. 10 and 11.

Figure 10:
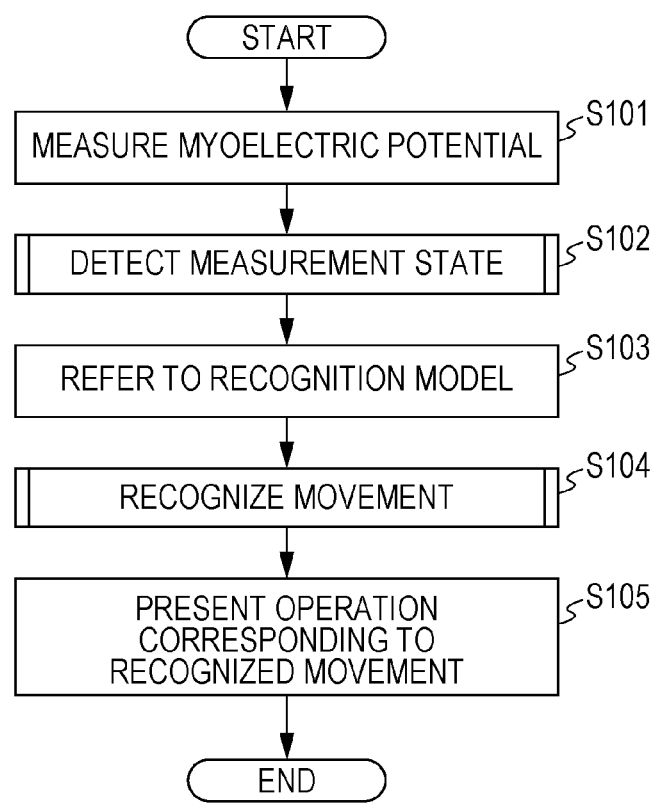
FIG. 10 is a flowchart depicting an operation of the myoelectric potential measurement device in Embodiment 1.

FIG. 10 is a flowchart depicting an operation of the myoelectric potential measurement device 110a in Embodiment 1 of the present disclosure.

First, the electrode unit 101 measures myoelectric potentials that occur due to a movement, with the plurality of electrodes ch1 to ch8 (S101). This step S101 corresponds to a myoelectric potential measurement step in which the annular electrode unit having the plurality of electrodes that come into contact with the arm of the user is used to measure the myoelectric potential at each of the plurality of electrodes.

Next (or parallel with the aforementioned step S101), the measurement state detection unit 106 detects the direction of gravity in the myoelectric potential measurement device 110a to thereby detect the measurement state of the myoelectric potential measurement device 110a attached to the arm (S102). This step S102 corresponds to a measurement state detection step in which the state in which the myoelectric potentials are measured by the myoelectric potential measurement unit 102 is detected.

Figure 11:
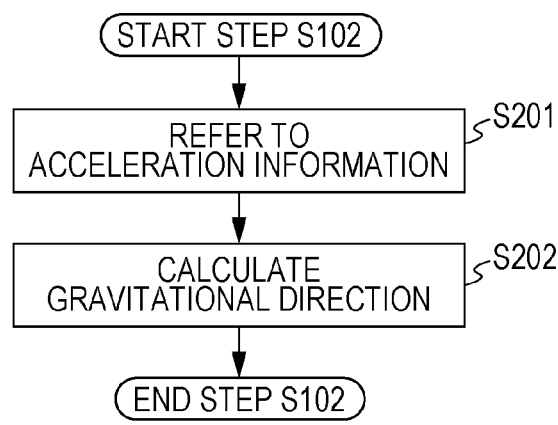
FIG. 11 is a flowchart depicting a detailed procedure for step S102 of FIG. 10.

FIG. 11 is a flowchart depicting a detailed procedure for step S102 (detection of the measurement state) of FIG. 10. The measurement state detection unit 106 refers to acceleration information obtained by the acceleration sensor provided therein (S201), and detects the myoelectric potential measurement state by calculating the gravitational direction in the myoelectric potential measurement device 110a from that acceleration information (S202).

Referring once again to FIG. 10, next, the movement recognition unit 104 refers to recognition models stored in the recognition model storage unit 103 (S103). The movement recognition unit 104 then recognizes a movement of the arm (S104). This step S104 corresponds to a movement recognition step in which a movement of the arm is recognized based on the myoelectric potentials measured in the myoelectric potential measurement step and the recognition result is output.

Figure 12:
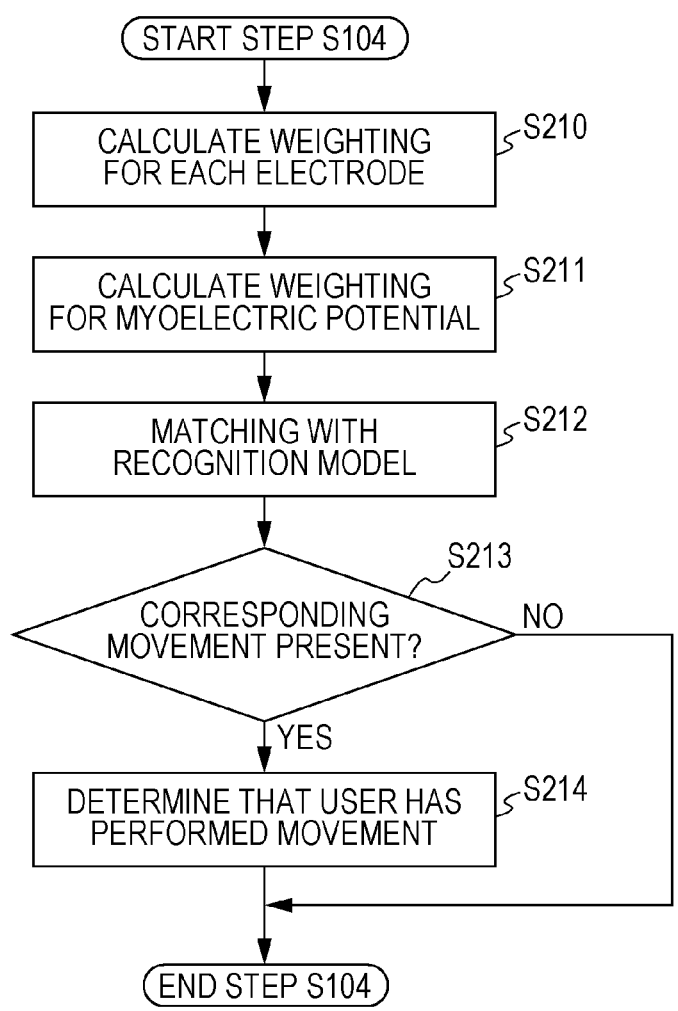
FIG. 12 is a flowchart depicting a detailed procedure for step S104 of FIG. 10.
Figure 14A:
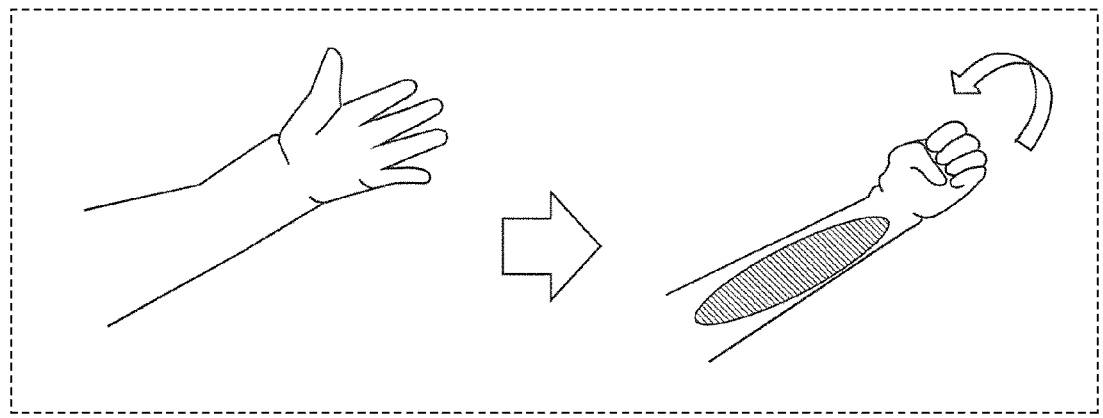
FIG. 14A is a drawing illustrating a movement that uses a muscle on the anterior side of an arm.
Figure 14B:
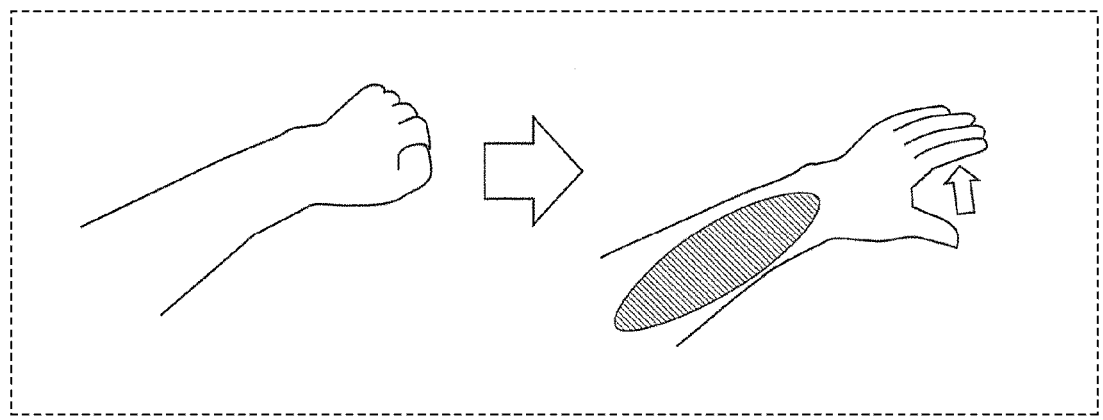
FIG. 14B is a drawing illustrating a movement that uses a muscle on the anterior side of an arm.

FIG. 12 is a flowchart depicting a detailed procedure for step S104 (movement recognition) of FIG. 10. First, as indicated by the aforementioned Expression 1, the movement recognition unit 104 calculates a weighting for each electrode ch1 to ch8 corresponding to the myoelectric potential measurement state (specifically, the direction of gravity in the myoelectric potential measurement device 110a) detected in step S102 (S210). Next, the movement recognition unit 104 performs a calculation in which the myoelectric potentials measured by the myoelectric potential measurement unit 102 are multiplied by the calculated weightings (S211). The movement recognition unit 104 then performs a matching calculation between the myoelectric potentials obtained by multiplying with the weightings and the referenced recognition models (S212). The movement recognition unit 104 thereby determines whether or not there is a corresponding movement among the plurality of types of arm movements registered as recognition models (S213).

A threshold value or the like is provided, for example, and a movement having a value with which the difference with a model is equal to or less than the predetermined threshold value is treated as a corresponding movement. As a result, the movement recognition unit 104 determines that the user has carried out a corresponding movement (S214) if it is determined that there is a corresponding movement (yes in S213), and, on the other hand, ends this processing (movement recognition) if it is determined that there is no corresponding movement (no in S213). In this way, in the movement recognition step (S104 in FIG. 10), preferred electrodes, which are electrodes having a portion of the arm positioned vertically thereunder, are specified from among the plurality of electrodes on the basis of the myoelectric potential measurement state detected in the measurement state detection step (S102), and a movement of the arm is recognized with the myoelectric potentials measured by the specified preferred electrodes having been prioritized over the myoelectric potentials measured by non-preferred electrodes, which are the electrodes other than the preferred electrodes.

Referring once again to FIG. 10, lastly, the presentation unit 105 displays the result of the movement recognition or an operation corresponding to the recognized movement on a screen and transmits an operation signal to the terminal (S105).

As described above, according to the present embodiment, a movement of the arm is recognized with myoelectric potentials measured by electrodes that are likely to be in close contact with the arm having being prioritized over myoelectric potentials measured by electrodes that are unlikely to be in close contact with the arm. Thus, a movement of the arm is recognized with myoelectric potentials being appropriately measured even when not all of the plurality of electrodes are in close contact with the arm.

In other words, in a user interface device which uses a myoelectric potential measurement device that attaches to an arm, when operations are to be input by moving a finger or a hand, it is often the case that certain fixed operations are carried out due to the structure of the human body. For example, when the arm is normally in a lowered state and some kind of operation is to be carried out, it is often the case that the arm is raised to near the chest, the presentation unit 105 is oriented to be visible to the user, and the hand is moved while the arm remains stationary. In such cases, as indicated in the present embodiment, that movement or angle or the like can be detected by an acceleration sensor or the like. By using this detected operation state to estimate the contact state of the electrodes of the myoelectric potential measurement device and carrying out recognition with greater precision, it becomes possible to easily carry out operations using myoelectric potentials even in an everyday environment.

Embodiment 2

Next, a myoelectric potential measurement device according to Embodiment 2 of the present disclosure will be described.

In the aforementioned Embodiment 1, the contact state of a myoelectric potential measurement device was estimated based on a measurement state detected by the measurement state detection unit 106 and measured myoelectric potentials were corrected; however, in addition thereto, the recognition model may be switched. Hereinafter, a description is given using the drawings.

FIG. 13 is a block diagram depicting the configuration of a myoelectric potential measurement device 110b in Embodiment 2 of the present disclosure. This myoelectric potential measurement device 110b is a device that measures a myoelectric potential of an arm of a user and recognizes a movement of the arm on the basis of that measurement result, and is provided with an electrode unit 101, a myoelectric potential measurement unit 102, a recognition model storage unit 103a, a movement recognition unit 104a, a presentation unit 105, and a measurement state detection unit 106. In this myoelectric potential measurement device 110b, the movement recognition unit 104 of the myoelectric potential measurement device 110a in Embodiment 1 is replaced by the movement recognition unit 104a, which has a recognition model switching unit 107, and the recognition model storage unit 103 of the myoelectric potential measurement device 110a is replaced by the recognition model storage unit 103a, which has a plurality of recognition models including a first recognition model 108 and a second recognition model 109. In other words, the myoelectric potential measurement device 110b of the present embodiment is also provided with a function relating to switching recognition models in addition to the functions provided in the myoelectric potential measurement device 110a of Embodiment 1. Hereinafter, constituent elements that are the same as in Embodiment 1 are denoted by the same reference characters and descriptions thereof are omitted, and a description is given focusing on the differences.

When a finger or a hand is moved, the muscles that are activated are more or less decided due to the structure of the human body, and consequently there are arm movements that are easy to recognize by the positions of electrodes and there are arm movements that are not. FIGS. 14A, 14B, 15A, and 15B are drawings illustrating the relationship between a movement of an arm and a myoelectric potential. As with the movement depicted in FIG. 14A, when transitioning from a state in which the fingers are extended to the fingers being bent, the muscles of the anterior side of the arm (the hatching section in the right portion of FIG. 14A) contract and a main action potential (myoelectric potential) occurs. Meanwhile, as with the movement depicted in FIG. 14B, for example, when transitioning from a state in which the fingers are bent to the fingers being extended, the muscles of the posterior side of the arm (the hatching section in the right portion of FIG. 14B) contract and a main action potential occurs.

Consequently, in the case where the movement used when transitioning from a state in which the fingers are bent to the fingers being extended is to be a recognition target, for example, the myoelectric potentials measured by the electrodes positioned on the posterior side exhibit a greater change and are easy to detect. Meanwhile, in the case where the movement used when transitioning from a state in which the fingers are extended to the fingers being bent is a movement that is to be recognized, conversely, myoelectric potentials that exhibit a greater change are likely to occur at the electrodes positioned on the anterior side.

Figure 15A:
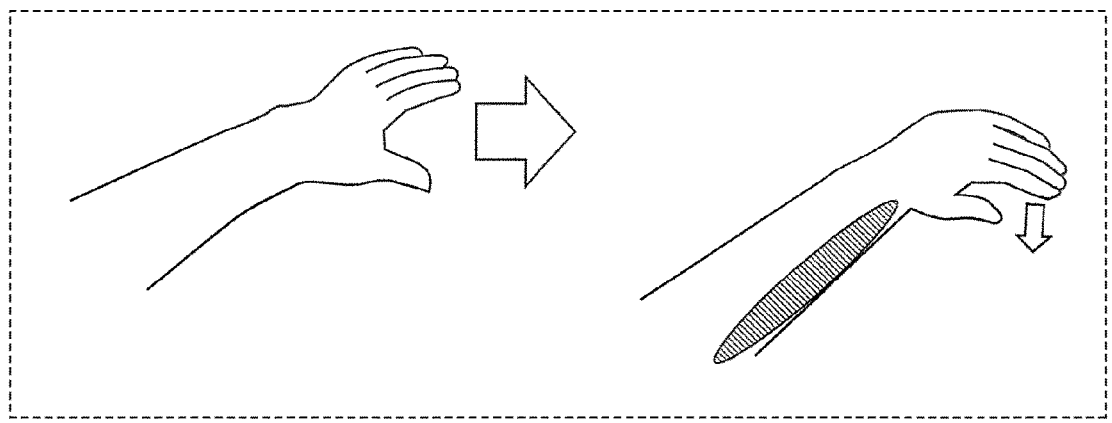
FIG. 15A is a drawing illustrating a movement that uses a muscle on the posterior side of an arm.
Figure 15B:
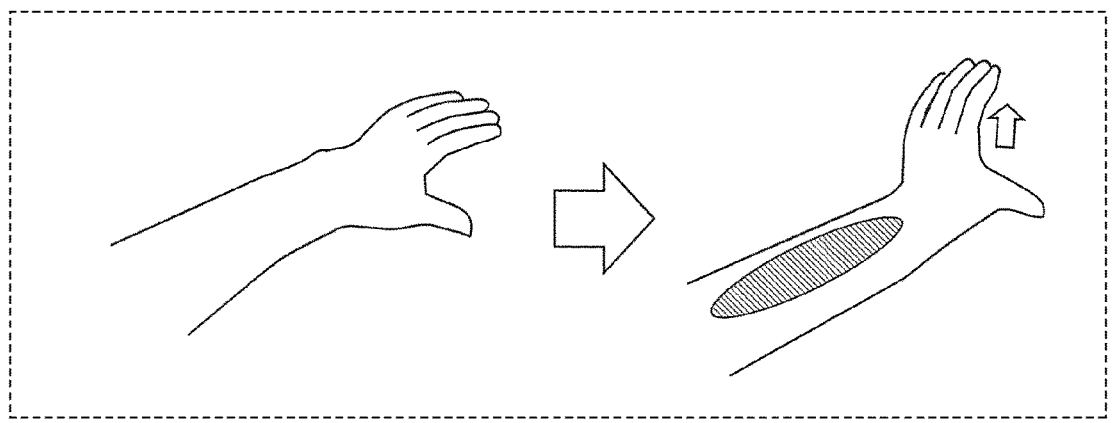
FIG. 15B is a drawing illustrating a movement that uses a muscle on the posterior side of an arm.

Similarly, as with the movement depicted in FIG. 15A, when the fingers are bent to the inside (anterior side), the muscles of the anterior side of the arm (the hatching section in the right portion of FIG. 15A) contract and an action potential (myoelectric potential) is mainly generated. Meanwhile, when the fingers are moved to the posterior side, the muscles of the posterior side of the arm (the hatching section in the right portion of FIG. 15B) contract and a large action potential (myoelectric potential) is generated. Consequently, it is easier for the electrodes on the side corresponding to the respective movement to detect changes in the myoelectric potentials. In addition, it is also easier for the electrodes positioned on the side corresponding to the respective movement to detect changes in the myoelectric potentials that accompany extremely small movements such as only the index finger being inclined to the inside, not only the magnitude of a myoelectric potential. In the present embodiment, positions at which it is easy for myoelectric potentials to be measured are taken into consideration, and separate recognition models are used to recognize arm movements.

FIG. 16 and FIG. 17 are drawings respectively depicting examples of the first recognition model 108 and the second recognition model 109 stored in the recognition model storage unit 103a. For example, the first recognition model 108 indicates myoelectric potential change patterns for an arm movement with which anterior-side myoelectric potentials are likely to occur. FIG. 16 is a drawing depicting an example of the first recognition model 108 stored in the recognition model storage unit 103a. Here, for example, the movement from an "open hand state (paper)" to a "clenched state (rock)" is stored as one recognition model (11), and is stored as an "activate application" operation (terminal operation), for example.

Meanwhile, the second recognition model 109 indicates myoelectric potential change patterns for an arm movement with which posterior-side myoelectric potentials are likely to occur. FIG. 17 is a drawing depicting an example of the second recognition model 109 stored in the recognition model storage unit 103a. Here, for example, the movement from a "clenched state (rock)" to an "open hand state (paper)" is stored as one recognition model (21) accompanied by a "forward one song" operation (terminal operation), for example.

The movement recognition unit 104a includes the recognition model switching unit 107 in addition to the functions of the movement recognition unit 104 in Embodiment 1. The recognition model switching unit 107 is a processing unit that switches the recognition model to be used (selects one recognition model from a plurality of recognition models), on the basis of the measurement state detected by the measurement state detection unit 106. For example, as indicated in Embodiment 1, it is possible for the measurement state detection unit 106 to detect which side of the arm is oriented upward on the basis of the direction of gravity, from acceleration information from when the arm is raised. Thus, the recognition model switching unit 107 switches the recognition model to be used on the basis of this information, and the movement recognition unit 104*a* thereby carries out movement recognition with greater precision. In other words, the movement recognition unit 104*a* uses the recognition model selected by the recognition model switching unit 107 to recognize a movement of the arm.

Next, a description will be given regarding an operation (myoelectric potential measurement method) of the myoelectric potential measurement device 110*b* in the present embodiment configured as described above.

Figure 18:
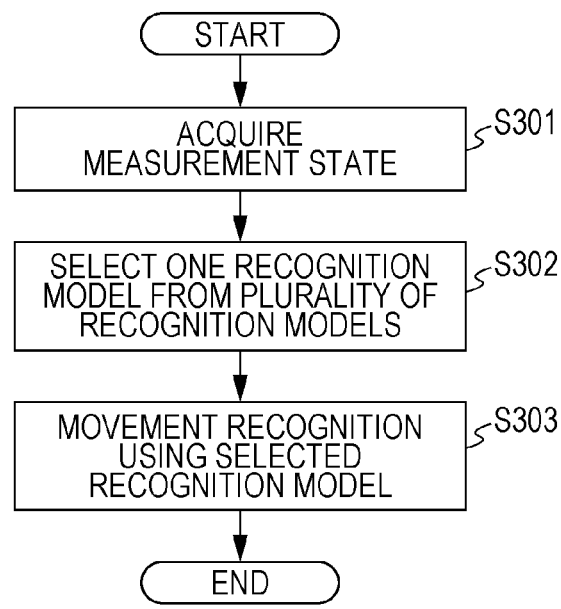
FIG. 18 is a flowchart depicting an operation of the myoelectric potential measurement device in Embodiment 2.

FIG. 18 is a flowchart depicting an operation of the myoelectric potential measurement device 110*b* in the present embodiment. The movement recognition unit 104*a* acquires a measurement state by the measurement state detection unit 106 (S301). The recognition model switching unit 107 of the movement recognition unit 104*a* then selects one recognition model from the plurality of recognition models stored in the recognition model storage unit 103*a*, on the basis of the acquired measurement state. (S302). Lastly, the movement recognition unit 104*a* uses the recognition model selected by the recognition model switching unit 107 to recognize a movement of the arm by way of the same procedure (steps S210 to S214 of FIG. 12) as in Embodiment 1 (S303).

Figure 19A:
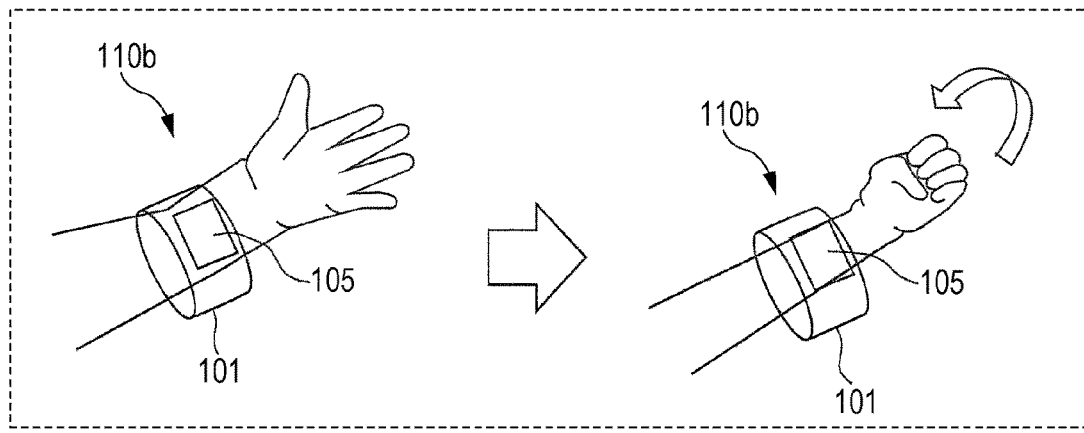
FIG. 19A is a drawing depicting an example of movement recognition by a movement recognition unit of the same myoelectric potential measurement device.
Figure 19B:
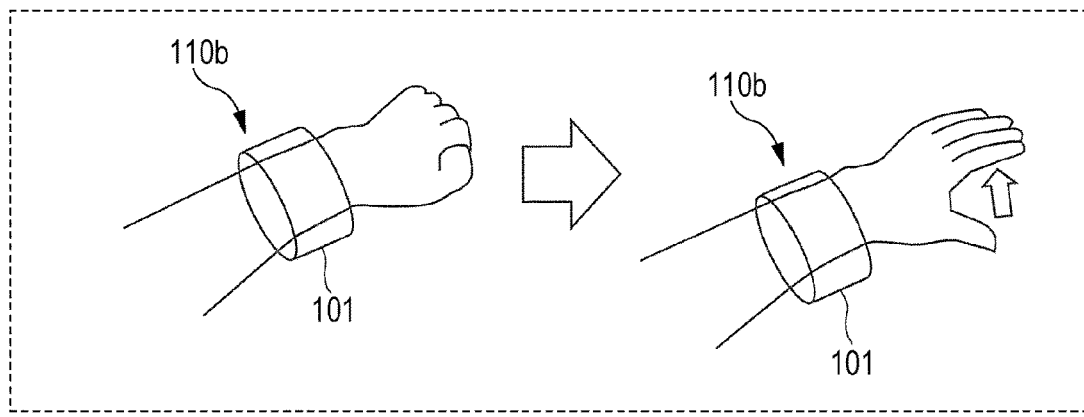
FIG. 19B is a drawing depicting an example of movement recognition by the movement recognition unit of the same myoelectric potential measurement device.

FIGS. 19A and 19B are drawings depicting an example of the movement recognition performed by the movement recognition unit 104*a*. Here, as depicted in FIGS. 16 and 17, the first recognition model 108 indicates myoelectric potential change patterns for an arm movement with which anterior-side myoelectric potentials are likely to occur, and, meanwhile, the second recognition model 109 indicates myoelectric potential change patterns for an arm movement with which posterior-side myoelectric potentials are likely to occur.

For example, when the user has oriented the anterior side upward as depicted in FIG. 19A, the recognition model switching unit 107 selects the recognition model for a movement with which anterior-side myoelectricity is likely to occur (the first recognition model 108). As a result, the movement recognition unit 104*a* uses the selected first recognition model 108 to carry out arm movement recognition. Meanwhile, when the user has oriented the posterior side upward as depicted in FIG. 19B, the recognition model switching unit 107 selects the recognition model for a movement with which posterior-side myoelectricity is likely to occur (the second recognition model 109). As a result, the movement recognition unit 104*a* uses the selected second recognition model 109 to carry out arm movement recognition. Thus, it becomes possible to realize arm movement recognition that is robust with respect to noise.

It should be noted that the position of the presentation unit 105 on the arm and the attachment state of the myoelectric potential measurement device 110*b* may be taken into consideration when switching the recognition model. Up to here, in Embodiments 1 and 2, a description has been given using an example in which the myoelectric potential measurement device 110*b* is attached in such a way that the presentation unit 105 is positioned on the anterior side; however, there are numerous attachment states preferred by people such as positioning the presentation unit 105 on the posterior side. Furthermore, with regard to a myoelectric potential measurement device 110*b* such as that in the present embodiment that is attached to an arm, in the case where an operation for the myoelectric potential measurement device 110*b* itself is to be carried out, there are operations that have to be carried out while looking at the presentation unit 105 and there are operations for which it is not always necessary to look at the presentation unit 105. For example, although it is necessary to look at the presentation unit 105 when selecting a song to be replayed from among a plurality of songs in the operation-target terminal, it is not always necessary to look at the presentation unit 105 when increasing the volume and so on.

Thus, the position of the presentation unit 105 on the arm and the attachment status may be taken into consideration when switching the recognition model. For example, input from the user is received depending on whether the myoelectric potential measurement device 110*b* is attached in such a way that the presentation unit 105 is positioned on the posterior side or whether the myoelectric potential measurement device 110*b* is attached in such a way that the presentation unit 105 is positioned on the anterior side when the myoelectric potential measurement device 110*b* is attached. In this example, the measurement state detection unit 106 specifies the direction of gravity in the presentation unit 105 to thereby detect the measurement state.

Figure 20:
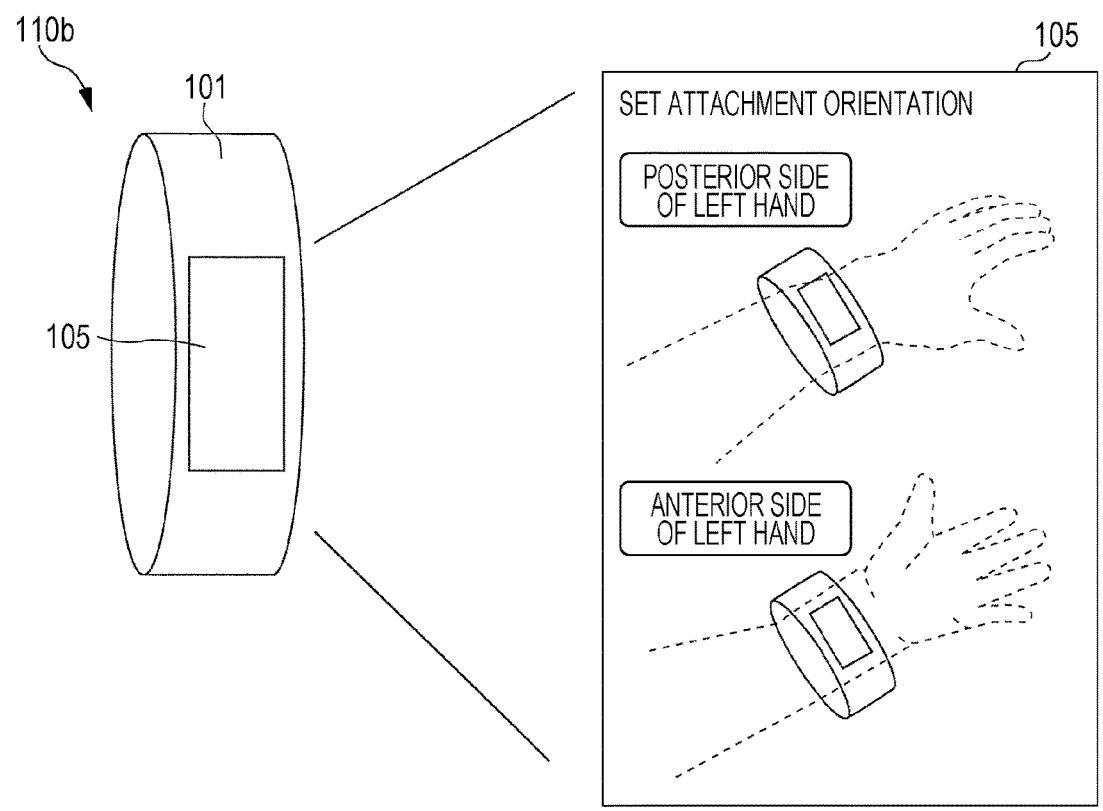
FIG. 20 is a drawing depicting an example of an operation of the myoelectric potential measurement device in which the recognition model is switched depending on the position of a presentation unit on the arm.

FIG. 20 is a drawing depicting an example of such an operation in which the recognition model is switched depending on the position of the presentation unit 105 on the arm. Here, the recognition model is switched according to the side (posterior side or anterior side) on which the presentation unit 105 is positioned when the myoelectric potential measurement device 110*b* is attached. For example, when the presentation unit 105 is positioned on the posterior side and the user has performed a movement such as raising his/her arm to be able to see the presentation unit 105, the posterior side is in the opposite direction to gravity and those electrodes of the myoelectric potential measurement device 110*b* come into contact with the arm, and therefore the movement recognition unit 104*a* carries out movement recognition using the second recognition model 109, which is the preferred recognition model for movement recognition in which posterior-side myoelectric potentials are used.

Meanwhile, when the user has attached the myoelectric potential measurement device 110*b* in such a way that the presentation unit 105 is positioned on the anterior side and the user has performed a movement such as raising his/her arm to be able to see the presentation unit 105, the anterior side is in the opposite direction to gravity and those electrodes of the myoelectric potential measurement device 110*b* come into contact with the arm, and therefore the movement recognition unit 104*a* carries out movement recognition using the first recognition model 108, which is the preferred recognition model for movement recognition in which anterior-side myoelectric potentials are used. Thus, a myoelectric operation corresponding to the attachment implemented by the user becomes possible.

In the aforementioned example, an explanation was given using an example in which the specifying of whether the presentation unit 105 is positioned on the posterior side or the anterior side is carried out by way of user input; however, it should be noted that the present disclosure is not limited thereto. For example, it is also possible for detection to be made from a change in acceleration or a change in angular velocity. A method for specifying whether the presentation unit 105 is positioned on the posterior side or the anterior side will be described using FIGS. 21A to 21E and FIGS. 22A to 22E.

Figure 21A:
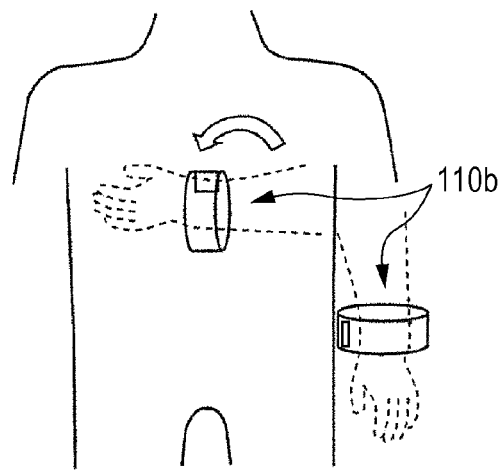
FIG. 21A is a drawing illustrating an example of the detection of a measurement state when the myoelectric potential measurement device has been attached in such a way that the presentation unit is positioned on the anterior side.
Figure 21B:
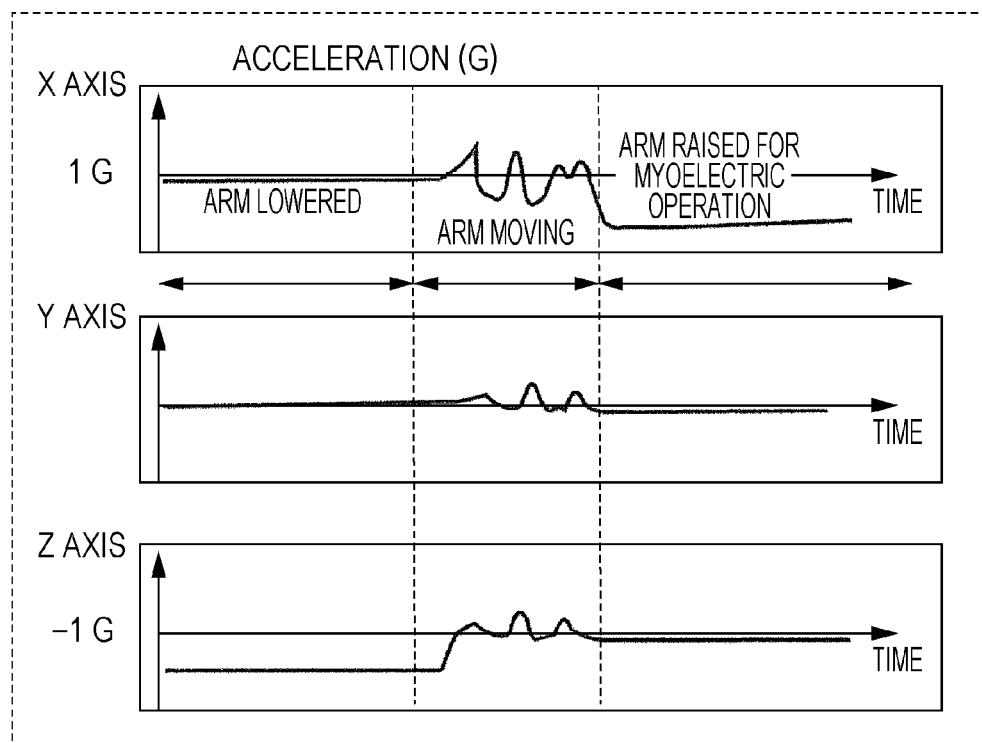
FIG. 21B is a drawing illustrating an example of the measurement of acceleration when the myoelectric potential measurement device has been attached in such a way that the presentation unit is positioned on the anterior side.
Figure 21C:
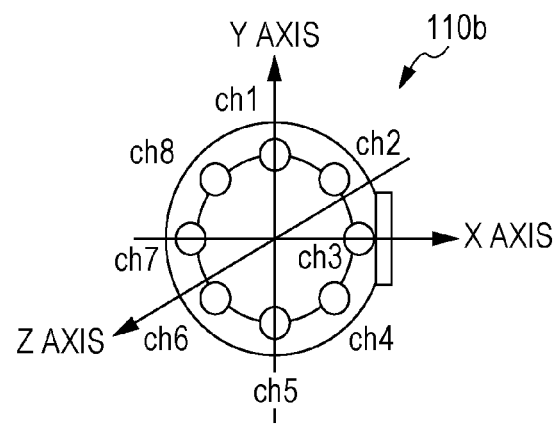
FIG. 21C is a drawing illustrating an example of the detection of a measurement state when the myoelectric potential measurement device has been attached in such a way that the presentation unit is positioned on the anterior side.
Figure 21D:
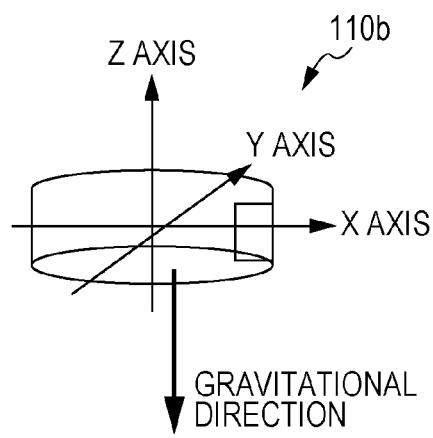
FIG. 21D is a drawing illustrating an example of the detection of a measurement state when the myoelectric potential measurement device has been attached in such a way that the presentation unit is positioned on the anterior side.
Figure 21E:
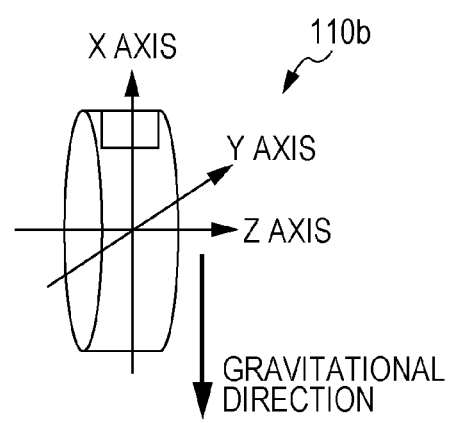
FIG. 21E is a drawing illustrating an example of the detection of a measurement state when the myoelectric potential measurement device has been attached in such a way that the presentation unit is positioned on the anterior side.
Figure 22A:
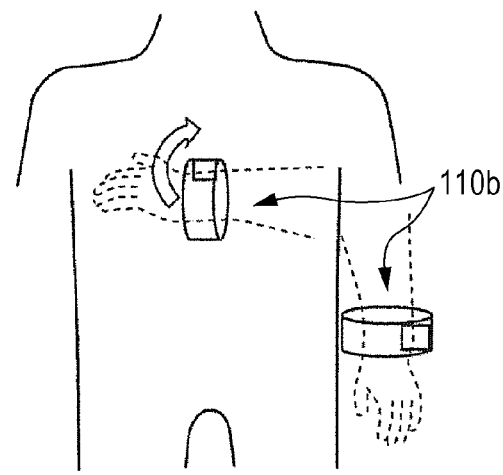
FIG. 22A is a drawing illustrating an example of the detection of a measurement state when the myoelectric potential measurement device has been attached in such a way that the presentation unit is positioned on the posterior side.
Figure 22B:
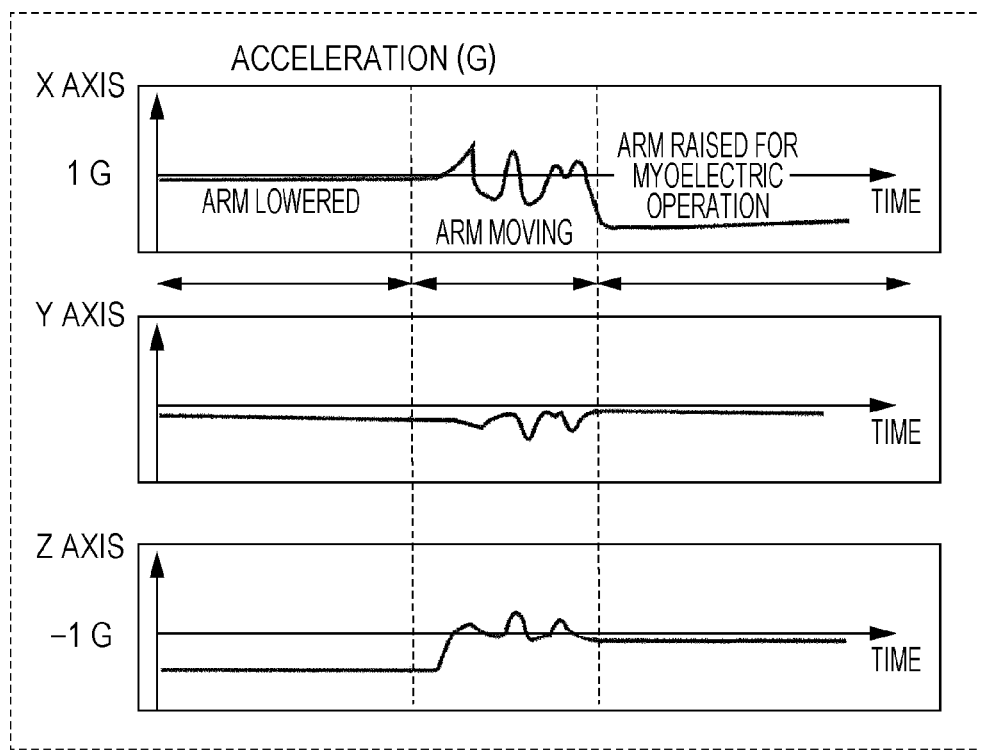
FIG. 22B is a drawing illustrating an example of the measurement of acceleration when the myoelectric potential measurement device has been attached in such a way that the presentation unit is positioned on the posterior side.
Figure 22C:
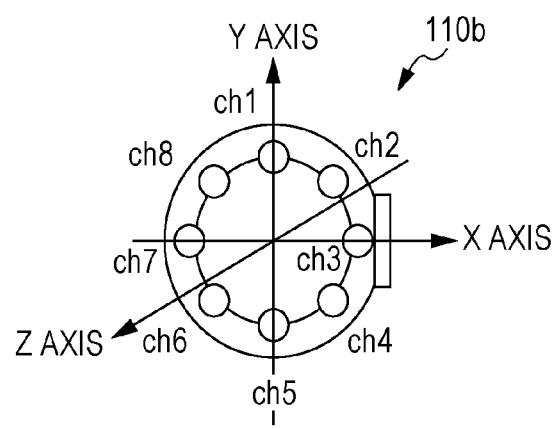
FIG. 22C is a drawing illustrating an example of the detection of a measurement state when the myoelectric potential measurement device has been attached in such a way that the presentation unit is positioned on the posterior side.
Figure 22D:
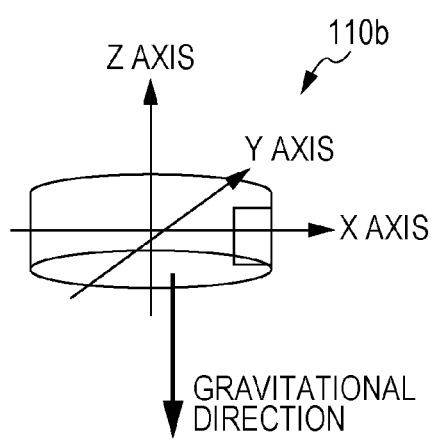
FIG. 22D is a drawing illustrating an example of the detection of a measurement state when the myoelectric potential measurement device has been attached in such a way that the presentation unit is positioned on the posterior side.
Figure 22E:
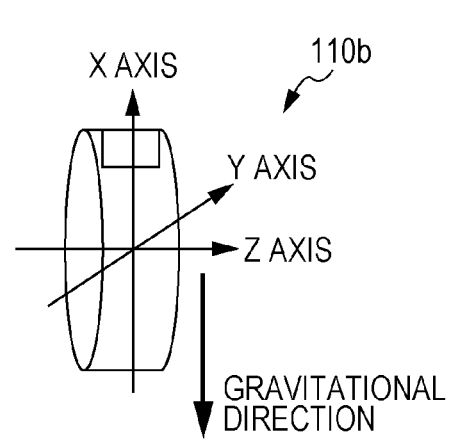
FIG. 22E is a drawing illustrating an example of the detection of a measurement state when the myoelectric potential measurement device has been attached in such a way that the presentation unit is positioned on the posterior side.

First, when the user moves his/her arm from a lowered state to a raised state, it is possible to detect not only a change in the direction of gravity but also a change as to whether the hand has turned to the inside or whether the hand has turned to the outside from the acceleration or the angular velocity. For example, in the case where the myoelectric potential measurement device 110*b* has been attached in such a way that the presentation unit 105 is positioned on the anterior side as depicted in FIG. 21A, when the arm is raised from a lowered state, the user turns the wrist from the inside to the outside in order to see the presentation unit 105. Meanwhile, in the case where the myoelectric potential measurement device 110*b* has been attached in such a way that the presentation unit 105 is positioned on the posterior side as depicted in FIG. 22A, when the arm is raised from a lowered state, the user turns the wrist from the outside to the inside in order to see the presentation unit 105. It is possible for this change to be detected by the measurement state detection unit 106 using the acceleration or the angular velocity, and for the attachment state of the myoelectric potential measurement device 110*b* to be detected.

Figure 23:
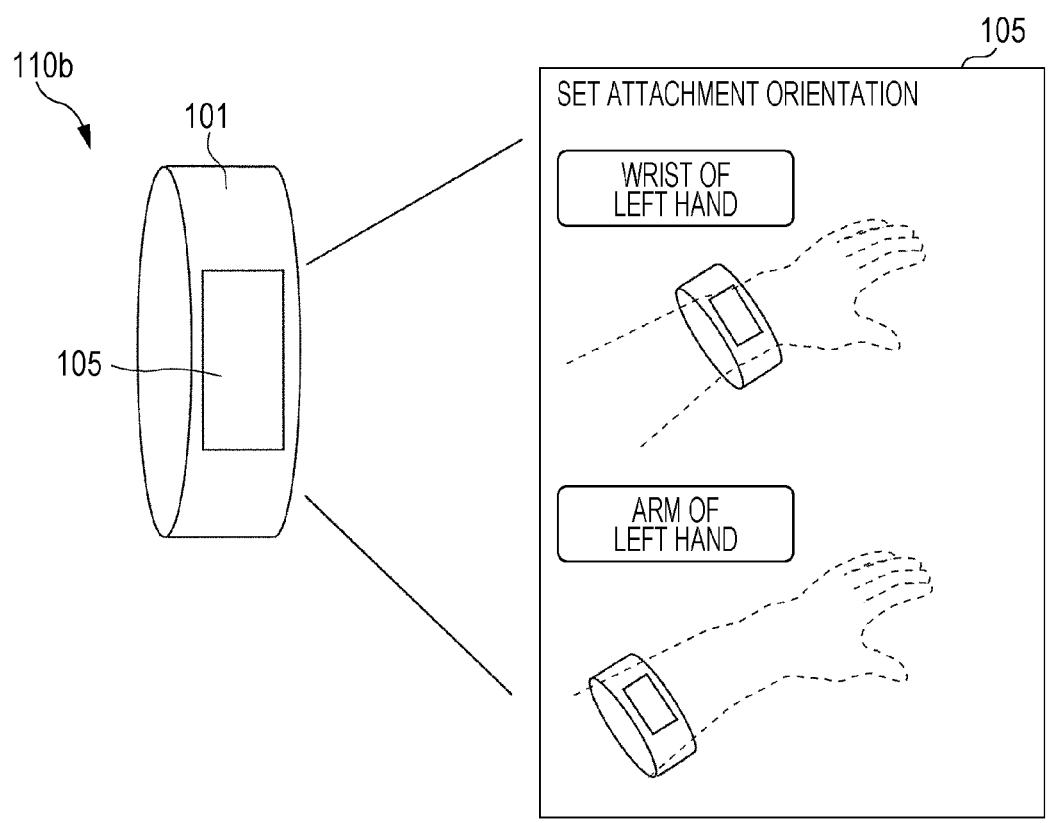
FIG. 23 is a drawing illustrating a case where the attachment position of the myoelectric potential measurement device is received by user input.

In the aforementioned example, an explanation was given using an example in which control switching is carried out according to whether the position of the presentation unit 105 when the myoelectric potential measurement device 110*b* is attached to the wrist is posterior or anterior; however, it should be noted that, in addition, the recognition model may be switched according to whether the attachment position is in the lower portion of the arm that includes the wrist or in the upper portion of the arm. For example, as depicted in FIG. 23, the myoelectric potential measurement device 110*b* receives the attachment position of the myoelectric potential measurement device 110*b* by user input. The myoelectric potential measurement device 110*b* then switches the recognition model according to this attachment position.

When the attachment position is in the lower portion of the arm such as the wrist, the gap between the myoelectric potential measurement device 110*b* and the arm becomes large, and there are cases where the electrodes of the myoelectric potential measurement device 110*b* do not make contact. Contrastingly, when the attachment position is in the upper portion of the arm (here, a position close to the elbow within the forearm), the gap between the myoelectric potential measurement device 110*b* and the arm becomes comparatively small, and there are cases where the electrodes of the myoelectric potential measurement device 110*b* all come into contact with the arm or there is a decrease in the number of the electrodes that do not make contact.

Furthermore, due to the characteristics of the human body, myoelectric potentials that accompany a movement of the hand or the wrist exhibit larger changes and finer changes in the upper portion of the arm, and therefore there are cases where recognition is easier with the upper portion of the arm. Thus, for example, when the attachment position of the myoelectric potential measurement device 110*b* is in the lower portion of the arm such as the wrist, recognition models having few recognition-target movements registered may be selected and recognition models having only comparatively large movements such as "rock to paper" registered may be selected. Meanwhile, for example, when the myoelectric potential measurement device 110*b* is attached in the upper portion of the arm, recognition models having comparatively fine movements such as a "finger movement" or a "number of fingers (one finger, two fingers)" registered may be selected, and the recognition model to be used may thereby be switched.

Furthermore, a circuit that measures contact impedance may be provided in the electrode unit 101 of the myoelectric potential measurement device 110*b*, and the attachment position of the myoelectric potential measurement device 110*b* may be detected by detecting the contact state between each electrode and the arm. For example, by measuring the contact impedance, it is possible to determine that the myoelectric potential measurement device 110*b* is attached to the wrist if it is detected that there is a predetermined number of electrodes with which there is no contact or insufficient contact, and, conversely, it is possible to determine that the myoelectric potential measurement device 110*b* is attached to the upper portion of the arm if all of the electrodes are making contact.

Figure 24A:
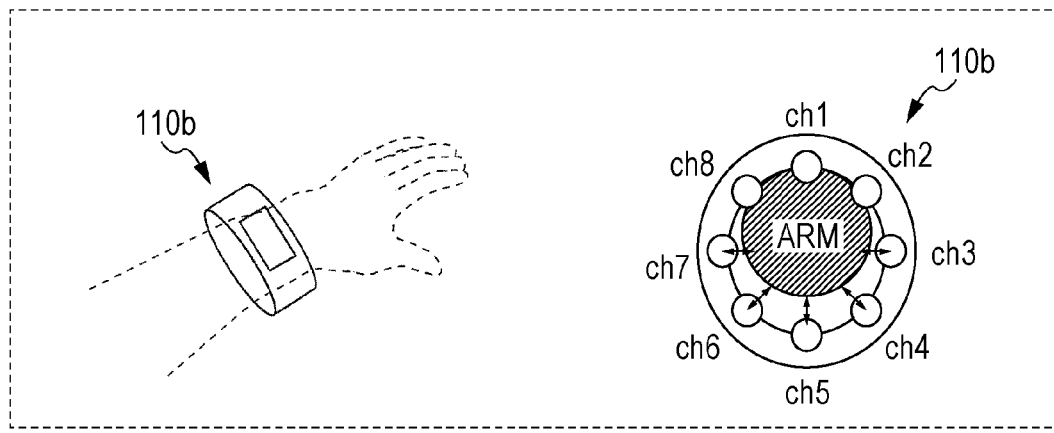
FIG. 24A is a drawing illustrating an example in which movement recognition is started according to the attachment state of the myoelectric potential measurement device.
Figure 24B:
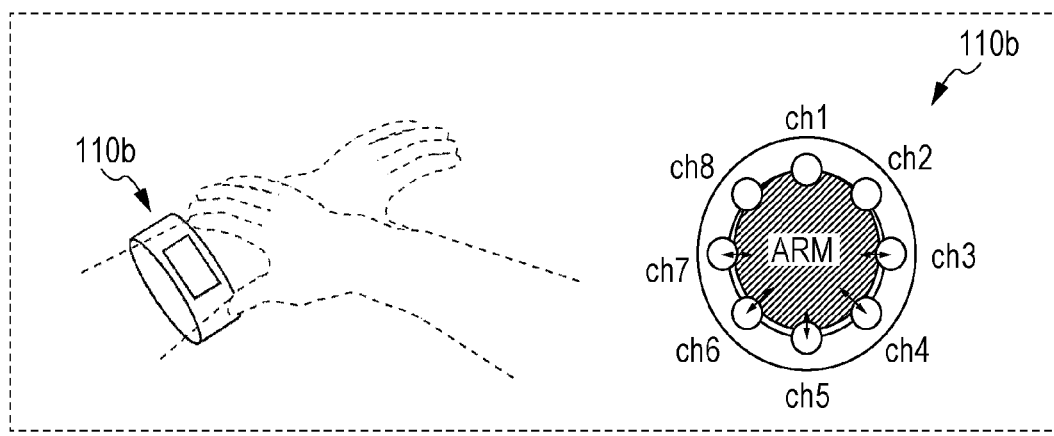
FIG. 24B is a drawing illustrating an example in which movement recognition is started according to the attachment state of the myoelectric potential measurement device.
Figure 24C:
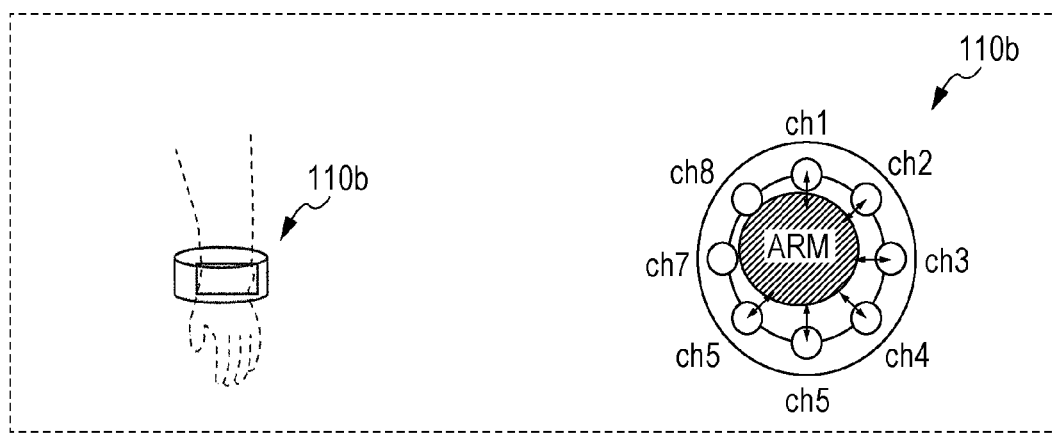
FIG. 24C is a drawing illustrating an example in which movement recognition is started according to the attachment state of the myoelectric potential measurement device.

Furthermore, movement recognition may be started using this kind of attachment state determination result as a trigger. For example, normally, as depicted in FIG. 24A, when the myoelectric potential measurement device 110*b* is attached like a wristwatch to the wrist and a myoelectric operation is required, it is possible for the recognition of myoelectricity to be handled by moving the myoelectric potential measurement device 110*b* to the upper portion of the arm as depicted in FIG. 24B and then returning the myoelectric potential measurement device 110*b* to the original wrist position as depicted in FIG. 24C when the myoelectric operation has ended. Thus, a myoelectric operation corresponding to an everyday usage scenario becomes possible.

Embodiment 3

Next, a myoelectric potential measurement device according to Embodiment 3 of the present disclosure will be described.

In Embodiment 1, a description was given regarding an example in which the myoelectric potential measurement state is detected using an acceleration sensor or the like and myoelectric potentials are corrected according to that measurement state. In the present embodiment, a description will be given regarding an example in which, in addition, by using an acceleration sensor or the like to specify the position of a myoelectric potential measurement device that is attached to a wrist of a user, arm movement recognition is carried out only when a myoelectric potential measurement device is in a specific spatial position with respect to the body of the user.

When the myoelectric potential measurement device is attached to a wrist and the user moves in an everyday manner, there are cases where movement recognition is executed when not intended by the user and an erroneous operation is caused. Thus, as a result of the myoelectric potential measurement device attached to the wrist executing movement recognition only when in a certain specific space with respect to the body of the user, the myoelectric potential measurement device is able to be used with no erroneous operations even when used in an everyday manner. Thus, in the present embodiment, a movement of the arm is recognized only when it is determined that the myoelectric potential measurement device is within a predetermined space.

Figure 25:
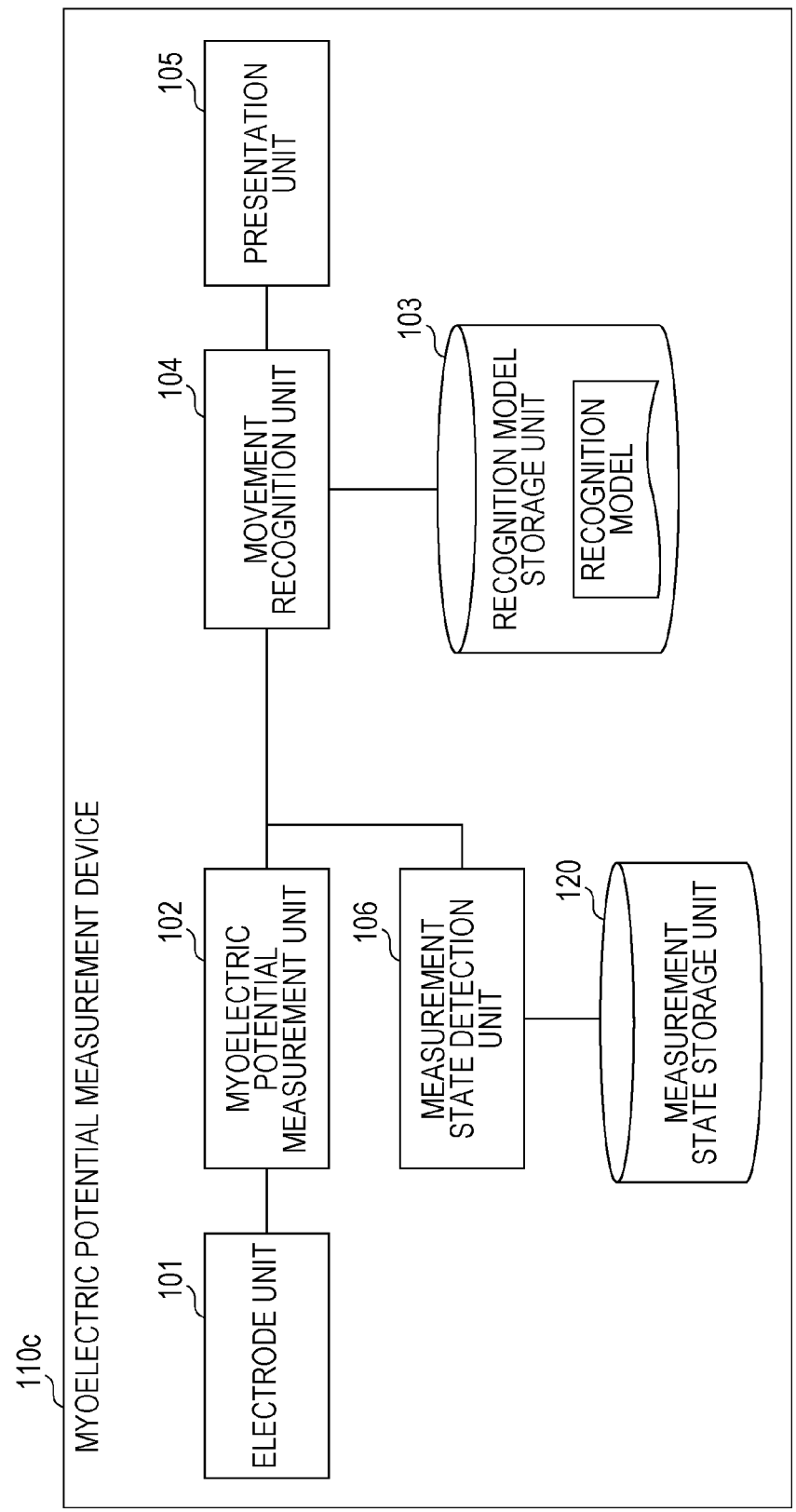
FIG. 25 is a block diagram depicting the configuration of a myoelectric potential measurement device in Embodiment 3.

FIG. 25 is a block diagram depicting the configuration of a myoelectric potential measurement device 110*c* in Embodiment 3 of the present disclosure. This myoelectric potential measurement device 110c is a device that measures a myoelectric potential of an arm of a user and recognizes a movement of the arm on the basis of a measurement result thereof, and is provided with an electrode unit 101, a myoelectric potential measurement unit 102, a recognition model storage unit 103, a movement recognition unit 104, a presentation unit 105, a measurement state detection unit 106, and a measurement state storage unit 120. This myoelectric potential measurement device 110c of FIG. 25 is provided with the measurement state storage unit 120 in addition to the constituent components provided in the myoelectric potential measurement device 110a of Embodiment 1. In other words, the myoelectric potential measurement device 110c of the present embodiment is also provided with a control function relating to the execution timing of movement recognition in addition to the functions provided in the myoelectric potential measurement device 110a of Embodiment 1. Hereinafter, constituent elements that are the same as in Embodiment 1 are denoted by the same reference characters and descriptions thereof are omitted, and a description is given regarding the differences.

The measurement state storage unit 120 is a storage device that stores changes that occur over time in a measurement state detected by the measurement state detection unit 106. In the present embodiment, the measurement state detection unit 106 stores repeatedly detected measurement states (changes that occur over time in a measurement state) in the measurement state storage unit 120. The movement recognition unit 104 then determines whether or not the wrist of the arm on which the myoelectric potential measurement device 110c is attached is within the predetermined space of the body of the user on the basis of the changes that occur over time in the measurement state stored in the measurement state storage unit 120, and recognizes a movement of the arm in accordance with the procedure (steps S210 to S214 of FIG. 12) in Embodiment 1 only when it is determined that the wrist is within the predetermined space. The predetermined space is a space that is set in a position that is higher than the elbow of the arm, for example.

Figure 26:
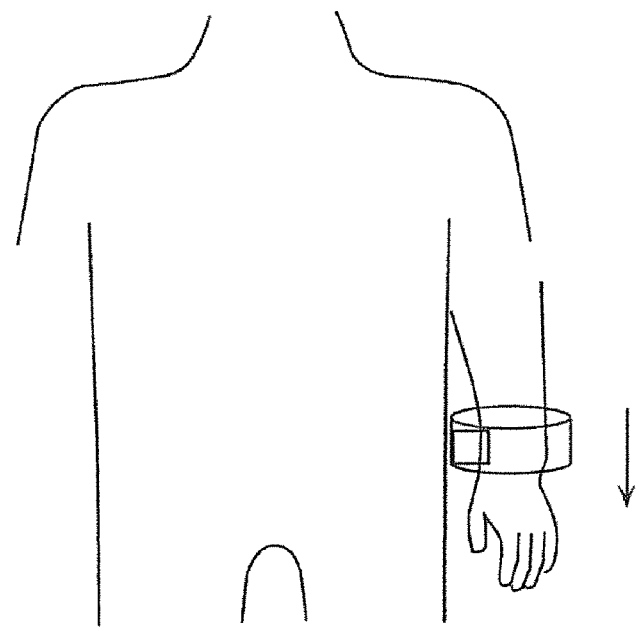
FIG. 26 is a drawing depicting an example of an attachment state of the myoelectric potential measurement device.

Generally, when the myoelectric potential measurement device is attached to the wrist, the wrist is often lower than the elbow during everyday activities, as depicted in FIG. 26. As a result, the gravitational direction in the myoelectric potential measurement device shifts due to gravity. Furthermore, the arm of the user generally becomes thinner toward the wrist, and therefore a gap often occurs between the myoelectric potential measurement device and the arm in this kind of state. As a result, measurement is often not possible even when an attempt is made to measure a finger movement or the like with the myoelectric potential measurement device in this state.

Figure 27:
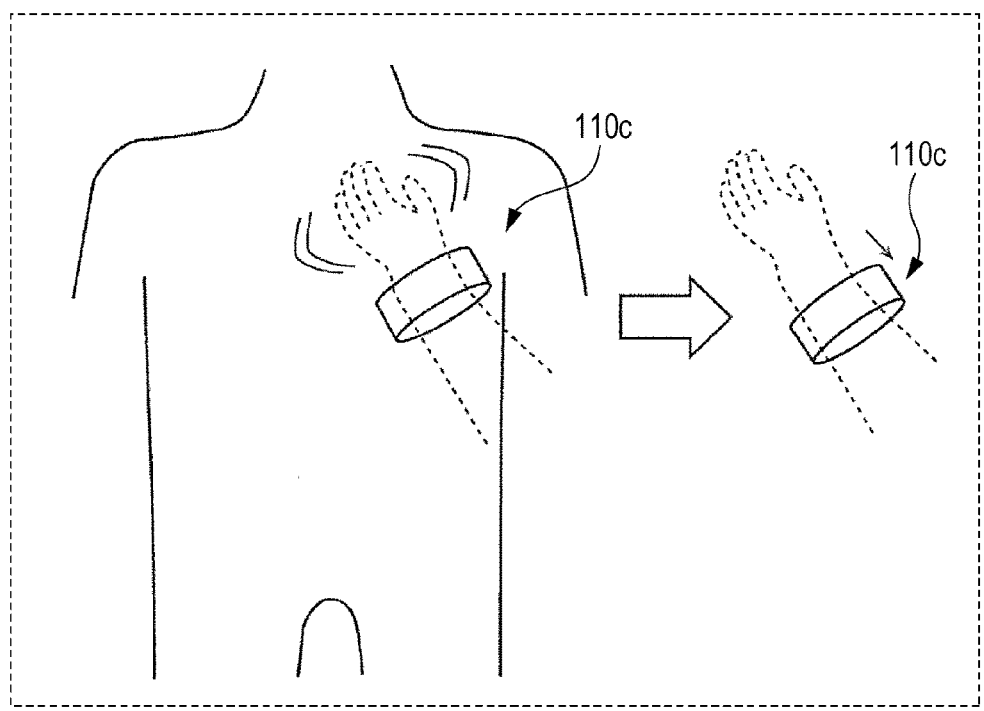
FIG. 27 is a drawing depicting an example of an attachment state of the myoelectric potential measurement device.
Figure 28:
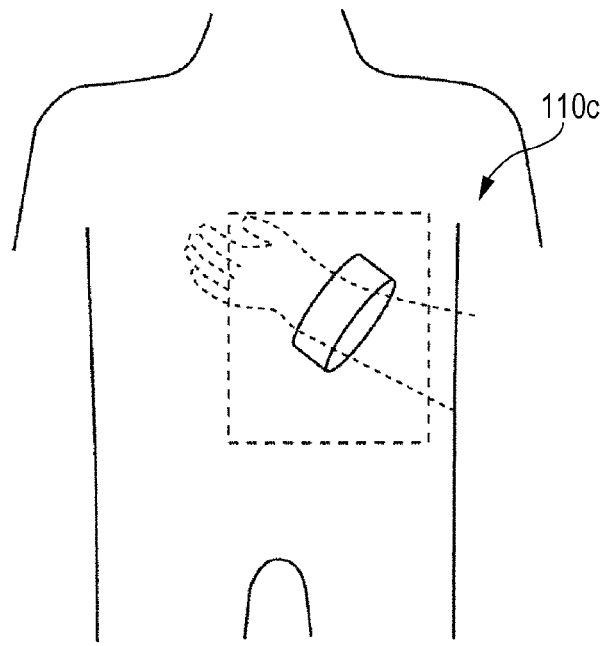
FIG. 28 is a drawing depicting an example of an attachment state of the myoelectric potential measurement device.

Thus, in the present embodiment, a movement of the user such as the following is used to execute movement recognition. In other words, in order to eliminate the gap between the myoelectric potential measurement device 110c and the arm with one hand, the user raises the wrist, to which the annular bracelet-type (for example, a shape such as a wristwatch) myoelectric potential measurement device 110c is attached, to be higher than the elbow and moves the wrist (shakes the wrist, for example) in such a way that gravity is thereby used to shift the myoelectric potential measurement device 110c toward the elbow, as depicted in FIG. 27. Next, by lowering the wrist slightly as depicted in FIG. 28, updating is performed to a mode in which movement recognition is carried out (in other words, the myoelectric potential measurement device 110c is caused to start movement recognition).

The gap between the myoelectric potential measurement device 110c and the arm is eliminated using this kind of movement. In addition, as depicted in FIG. 28, as a result of the movement recognition unit 104 executing movement recognition only when the wrist (namely, the myoelectric potential measurement device 110c) is in the predetermined space in front of the chest of the user, recognition is not carried out for hand gestures of the user when everyday movements are being carried out. Also, as a result of the myoelectric potential measurement device 110c carrying out movement recognition only when a transition is made from the movement depicted in FIG. 27 to the movement depicted in FIG. 28, it becomes possible to avoid erroneous operations. In other words, the movement recognition unit 104 recognizes a movement of the arm only when the wrist has entered the predetermined space after having been in a lowered state.

Figure 29:
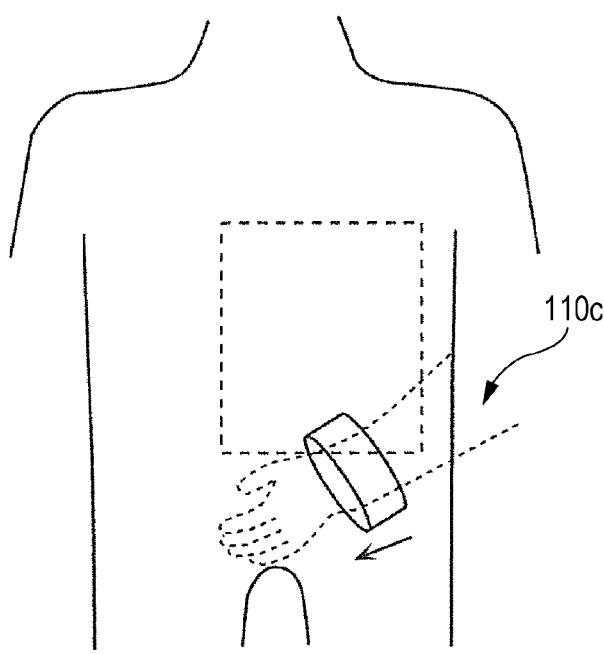
FIG. 29 is a drawing depicting an example of an attachment state of the myoelectric potential measurement device.

In addition, as depicted in FIG. 29, when the myoelectric potential measurement device 110c has moved outside of the space in which the myoelectric potential measurement device 110c carries out movement recognition, it is assumed that command input by the user has ended and the movement recognition unit 104 stops the movement recognition. Thereafter, the movement recognition unit 104 does not carry out movement recognition until there is once again a transition from the user performing the movement depicted in FIG. 27 to moving his/her wrist to the space in which movement recognition is carried out such as that depicted in FIG. 28.

Next, a description will be given regarding an operation (myoelectric potential measurement method) of the myoelectric potential measurement device 110c in the present embodiment configured as described above.

Figure 30:
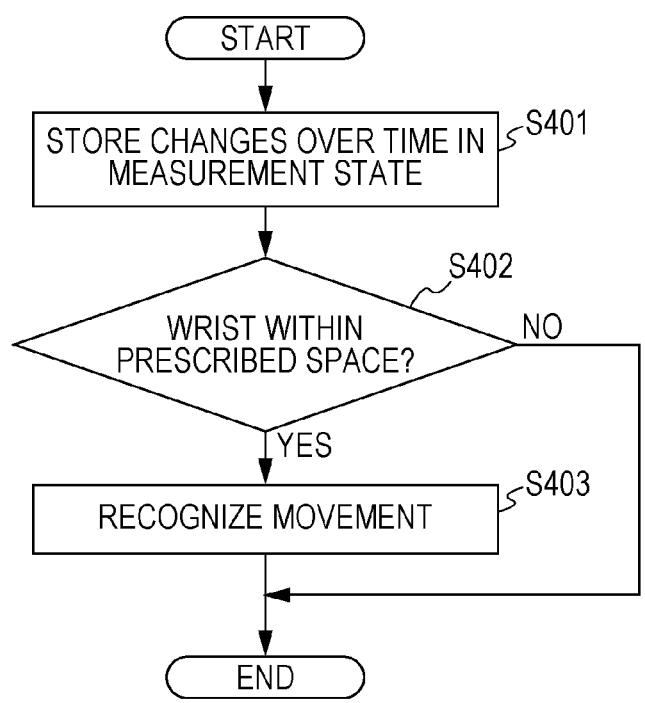
FIG. 30 is a flowchart depicting an operation of the myoelectric potential measurement device in Embodiment 3.
Figure 31:
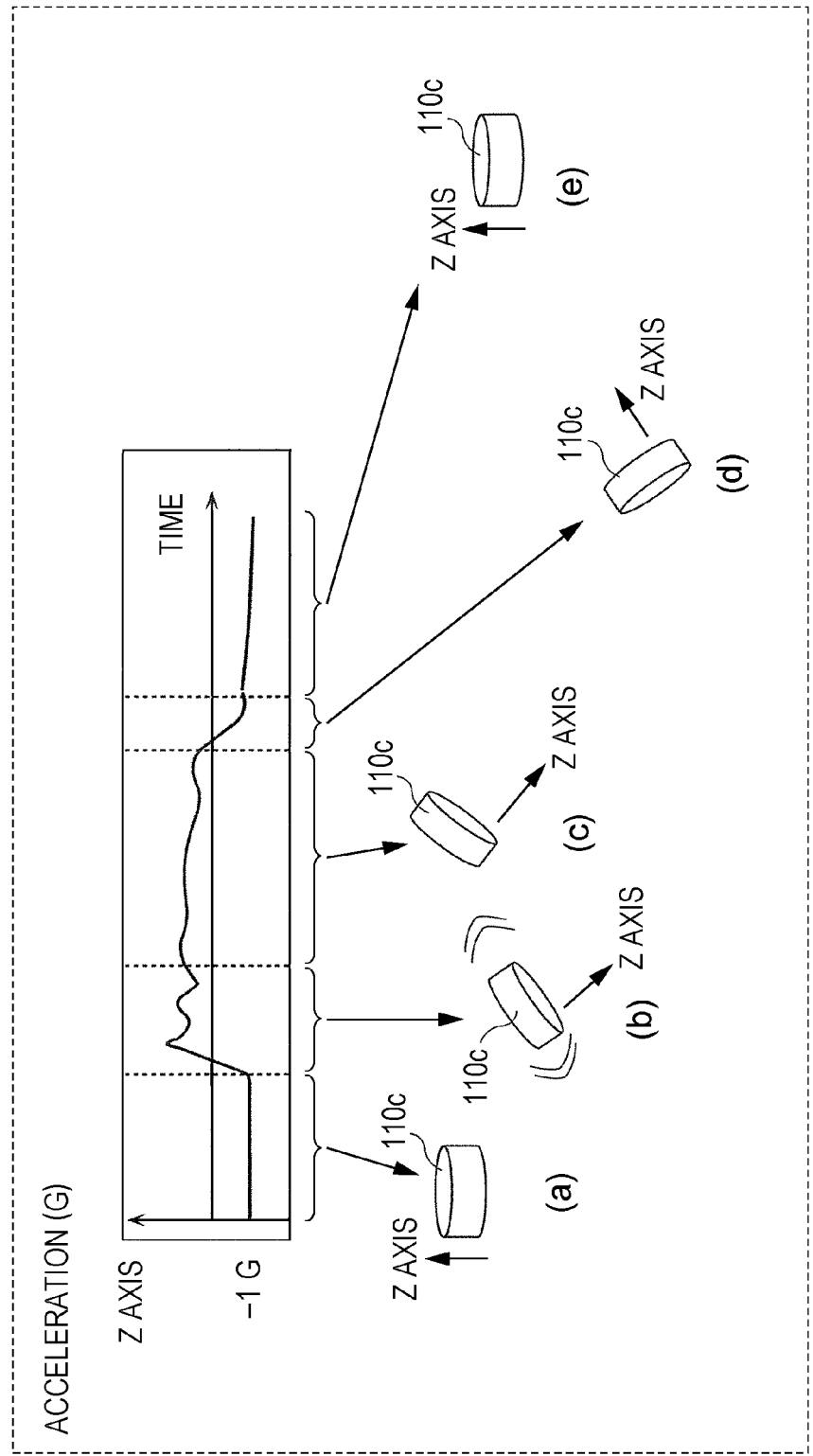
FIG. 31 is a drawing depicting a change in gravitational acceleration detected by a measurement state detection unit of the myoelectric potential measurement device.

FIG. 30 is a flowchart depicting an operation of the myoelectric potential measurement device 110c in the present embodiment. First, the measurement state detection unit 106 stores changes that occur over time in the detected measurement state in the measurement state storage unit 120 (S401). FIG. 31 depicts the states of gravitational acceleration detected by the measurement state detection unit 106 of the myoelectric potential measurement device 110c when the position of the myoelectric potential measurement device 110c has moved as depicted in FIG. 26 to FIG. 29. FIG. 31(*a*) depicts gravitational acceleration in a state in which the wrist is lowered, FIG. 31(*b*) depicts gravitational acceleration in a state in which the wrist is raised and shaken, FIG. 31(*c*) depicts gravitational acceleration in a state in which a gesture is being performed with the intention of performing an operation (recognition section), FIG. 31(*d*) depicts gravitational acceleration in a state in which the gesture has ended and the wrist is about to be lowered, and FIG. 31(*e*) depicts gravitational acceleration in a state in which the wrist is lowered. In the present embodiment, changes that occur over time in gravitational acceleration such as those depicted in FIG. 31 are detected by the measurement state detection unit 106 and stored in the measurement state storage unit 120.

Next, whenever a measurement state is stored in the measurement state storage unit 120 by the measurement state detection unit 106, the movement recognition unit 104 determines whether or not the wrist of the arm on which the myoelectric potential measurement device 110c is attached is within the predetermined space of the body of the user, on the basis of the changes that occur over time in the measurement state stored in the measurement state storage unit 120 (S402). If it is determined that the wrist is within the predetermined space (yes in S402), the movement of the arm is recognized using the same procedure (steps S210 to S214 of FIG. 12) as in Embodiment 1 (S403), and if it is not determined that the wrist is within the predetermined space (no in S402), the movement of the arm is not recognized (end).

For example, the movement recognition unit 104 recognizes a movement such as a movement of a finger of the user when a Z-axial gravitational acceleration component detected by the measurement state detection unit 106 has entered a predetermined range after the wrist has been raised from a lowered state and the myoelectric potential measurement device 110c has been shaken, as depicted in FIG. 31. It should be noted that the detection of these states becomes possible as a result of being measured as the direction (Z-axis direction) of gravitational acceleration in a plane parallel to the height direction of the body of the user by the measurement state detection unit 106, the gravitational acceleration being stored in the measurement state storage unit 120, and the movement recognition unit 104 thereby referring to the changes that occur over time in the measurement states stored in the measurement state storage unit 120. In addition, it should be noted that the measurement state detection unit 106 also measures the acceleration in the X-axis and Y-axis directions depicted in FIG. 21, thereby making it possible to further improve precision.

Figures 32, 33:
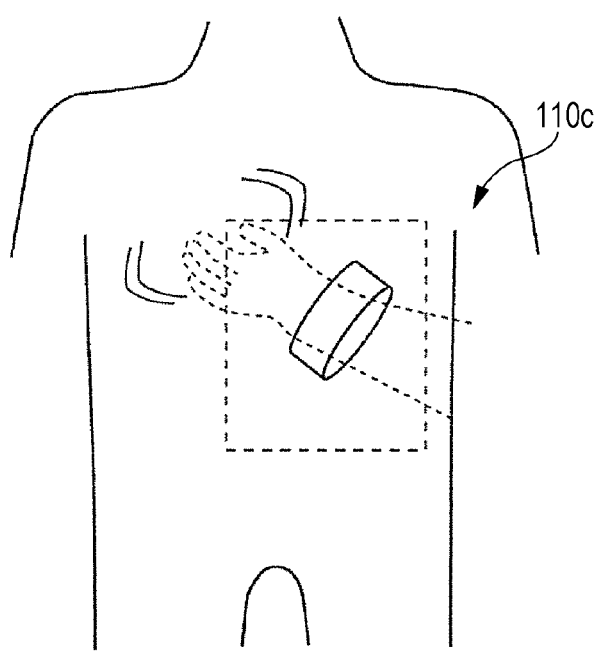
FIG. 32 is a drawing illustrating an operation of a movement recognition unit of the myoelectric potential measurement device.
FIG. 33 is a drawing depicting an example of an arm movement for when an operation input by the myoelectric potential measurement device is canceled.

In the present embodiment, as depicted in FIG. 32, the movement recognition unit 104 carries out arm movement recognition in the space in which the Z-axial direction gravitational acceleration detected by the measurement state detection unit 106 is 0.2 G to 0.8 G. This information (changes that occur over time in gravitational acceleration) is stored in the measurement state storage unit 120 of FIG. 25.

It should be noted that, for when the myoelectric potential measurement device 110c is positioned in the predetermined space for carrying out movement recognition as depicted in FIG. 33 and it is desirable for the immediately preceding operation input to be canceled, a recognition model may be stored in the recognition model storage unit 103 in such a way that cancellation is carried out by shaking the wrist in that space.

Furthermore, in the recognition model storage unit 103, the magnitude of the gravitational acceleration that defines the predetermined space depicted in FIG. 28 in which the myoelectric potential measurement device 110c is to carry out movement recognition may be determined by calibration, with the user who is to use the myoelectric potential measurement device 110c carrying out calibration or the like in advance in order to handle individual differences with regard to the predetermined space.

In this way, it becomes possible to input commands with few erroneous operations even in everyday life by, when the bracelet-type myoelectric potential measurement device 110c is attached, carrying out a movement such as the wrist being momentarily raised and the myoelectric potential measurement device 110c being brought into contact with skin, and then causing movement recognition to be carried out by the myoelectric potential measurement device 110c.

In the aforementioned example, a description was given with regard to the operation of the myoelectric potential measurement device 110c attached to the wrist, on the basis of a state in which the wrist is lowered during everyday life as depicted in FIG. 26; however, it should be noted that the present disclosure is not limited thereto. For example, when walking, a movement is made in which the wrist swings for a fixed time interval prior and subsequent to the wrist being in a lowered state. However, the wrist is often likewise positioned lower than the elbow in this case also. From a state such as this, there are cases where the user momentarily raises his/her wrist, shifts the myoelectric potential measurement device 110c toward the elbow, and carries out some kind of movement recognition, as in the movements depicted in FIG. 27 and FIG. 28. In such cases, a periodic movement of the user may be used to start movement recognition.

Figure 34:
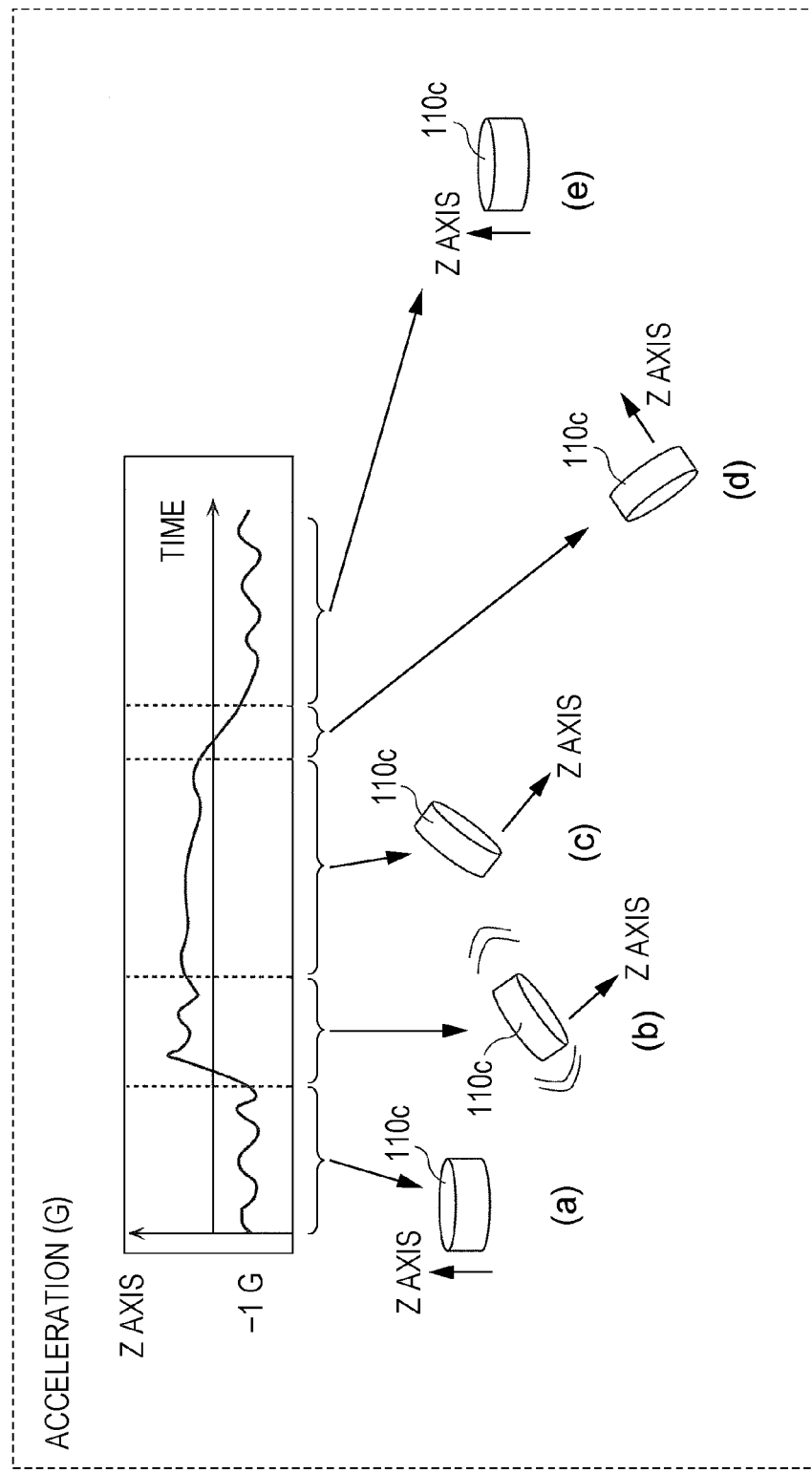
FIG. 34 is a drawing depicting a change in gravitational acceleration detected by the measurement state detection unit of the same myoelectric potential measurement device in the case where the user has carried out a periodic movement.

FIG. 34 is a drawing depicting gravitational acceleration (in other words, an example of a change over time in a measurement state stored in the measurement state storage unit 120) detected by the measurement state detection unit 106 when the user has carried out a periodic movement. FIG. 34(a) depicts gravitational acceleration in a state in which the wrist is lowered and the user is walking, FIG. 34(b) depicts gravitational acceleration in a state in which the wrist is raised and shaken, FIG. 34(c) depicts gravitational acceleration in a state in which a gesture is being performed with the intention of performing an operation (recognition section), FIG. 34(d) depicts gravitational acceleration in a state in which the gesture has ended and the user is walking once again, and FIG. 34(e) depicts gravitational acceleration in a state in which the wrist is lowered.

In this example, the user is walking with his/her wrist lowered, and changes that occur over time in gravitational acceleration indicating a periodic movement caused by walking are therefore detected. Thereafter, changes that occur over time in gravitational acceleration indicating a movement in which the wrist is raised and a myoelectric operation is about to be carried out (intentional operation) are detected. Thereafter, the wrist is lowered once again and walking is started. Changes that occur over time in gravitational acceleration such as these are detected by the measurement state detection unit 106 and stored in the measurement state storage unit 120. The movement recognition unit 104 then determines whether or not the wrist of the arm on which the myoelectric potential measurement device 110c is attached is within a predetermined space of the body of the user on the basis of the changes that occur over time in the measurement states stored in the measurement state storage unit 120, and recognizes a movement of the arm if it is determined that the wrist is within the predetermined space. In this example, the movement recognition unit 104 starts arm movement recognition at a timing at which the user raises his/her wrist and is about to carry out a myoelectric operation (intentional operation).

As described above, according to the present embodiment, arm movement recognition is started when the wrist has entered the predetermined space, and therefore the starting of movement recognition at an unintended timing is avoided. In other words, there are cases where, when the user moves in an everyday manner, the myoelectric potential measurement device 110c executes movement recognition when not intended by the user and an erroneous operation occurs. However, by detecting when the arm is raised to intentionally carry out an operation only when within a certain specific space with respect to the body of the user or by using changes from periodic movements and so forth, the myoelectric potential measurement device 110c can be used as a user interface device with no erroneous operations even when used in an everyday manner.

Descriptions have been given above based on Embodiments 1 to 3 regarding myoelectric potential measurement devices and myoelectric potential measurement methods according to the present disclosure; however, the present disclosure is not limited to these embodiments. Modes in which various modifications conceived by a person skilled in the art have been implemented in the present embodiments, and separate modes constructed by combining the constituent elements from different embodiments may also be included within the scope of one or more aspects of the present disclosure provided they do not depart from the purpose of the present disclosure.

For example, a myoelectric potential measurement device provided with all of the features (the measurement state detection unit 106, the movement recognition unit 104a, the recognition model storage unit 103a, and the measurement state storage unit 120) of the myoelectric potential measurement devices 110a to 110c in the aforementioned Embodiments 1 to 3 may also be included in the present disclosure.

Furthermore, in the aforementioned embodiments, each constituent element may be configured by using dedicated hardware, or may be realized by executing a software program suitable for each constituent element. Each constituent element may be realized by a program execution unit such as a CPU or a processor reading out and executing a software program recorded in a recording medium such as a hard disk or a semiconductor memory. Here, software that realizes a myoelectric potential measurement device of an aforementioned embodiment is a program such as the following.

In other words, this program includes, in a computer: a myoelectric potential measurement step in which an annular electrode unit 101 having a plurality of electrodes that come into contact with an arm of a user is used to measure a myoelectric potential at each of the plurality of electrodes; a movement recognition step in which a movement of the arm is recognized in accordance with the myoelectric potentials measured in the myoelectric potential measurement step, and a recognition result is output; and a measurement state detection step in which the state in which the myoelectric potentials are measured by a myoelectric potential measurement unit 102 is detected, with, in the movement recognition step, a preferred electrode, which is an electrode having a portion of the arm positioned vertically thereunder, being specified from among the plurality of electrodes in accordance with the measurement state detected in the measurement state detection step, and the movement of the arm being recognized with the myoelectric potential measured by the specified preferred electrode having been prioritized over the myoelectric potential measured by a non-preferred electrode, which is an electrode other than the preferred electrode.

Furthermore, although a presentation unit 105 is provided in the aforementioned Embodiments 1 to 3, the presentation unit 105 is not an essential constituent element. A result of the movement recognition performed by the movement recognition unit 104 may be output wirelessly, for example, to an external device.

Furthermore, although a measurement state storage unit 120 is provided in the aforementioned Embodiment 3, the measurement state storage unit 120 may not be provided. As long as the movement recognition unit 104 includes a memory that temporarily retains the measurement states detected by the measurement state detection unit 106, the same function as that in Embodiment 3 is able to be realized without the measurement state storage unit 120. At such time, in Embodiment 3, it is determined whether or not the wrist is within a predetermined space on the basis of changes that occur over time in the measurement state; however, the same determination may be carried out on the basis of a momentary measurement state. In other words, the myoelectric potential measurement device 110c may be provided with a table indicating determination references such as that depicted in FIG. 32, and the movement recognition unit 104 may determine whether or not the wrist is within the predetermined space in accordance with that table and in accordance with a momentary gravitational acceleration (Z-axis gravitational acceleration).

Furthermore, the present disclosure may be realized by a computer program or a digital signal being transmitted by way of a network represented by an electric telecommunication line, a wireless or wired telecommunication line, and the Internet.

Furthermore, the present disclosure may be a computer system provided with a microprocessor and a memory, in which the memory stores the computer program and the microprocessor operates according to the computer program.

Furthermore, the present disclosure may be carried out by another independent computer system as a result of the program or the digital signal being recorded on the recording medium and transferred, or as a result of the program or the digital signal being transferred by way of the network or the like.

In addition, the aforementioned embodiments and modified examples may be combined.

In the present disclosure, some or all of the units and devices, or some or all of the functional blocks of the block diagrams depicted in FIGS. 1, 13, and 25, may be executed by one or more electronic circuits including a semiconductor device, a semiconductor integrated circuit (IC), or a large-scale integration (LSI). An LSI or an IC may be integrated in one chip or may be configured with a plurality of chips being combined. For example, function blocks other than storage elements may be integrated in one chip. Here, reference has been made to an LSI and an IC; however, the name that is used differs depending on the degree of integration and these may be referred to as a system LSI, a very-large-scale integration (VLSI), or an ultra-large-scale integration (ULSI). A field-programmable gate array (FPGA) that is programmed after the manufacture of an LSI, or a reconfigurable logic device with which connection relationships inside an LSI can be reconfigured or circuit segments inside an LSI can be set up, is also able to be used for the same purpose.

In addition, it is possible for some or all of the functions or operations of the units or devices to be executed by software processing. In this case, software is be recorded in a non-transitory recording medium such as one or more ROMs, optical discs, or hard disk drives, and in the case where the software is to be executed by a processing device (processor), the software causes specific functions within the software to be executed by the processing device (processor) and peripheral devices. The system or the device may be provided with the one or more non-transitory recording mediums on which the software is recorded, the processing device (processor), and a required hardware device such as an interface.

The embodiments disclosed herein are exemplary in all aspects and should be considered to be non-limiting. The scope of the present disclosure is indicated by the scope of the patent claims not the aforementioned description, and is intended to include all alterations within a meaning and a scope equivalent to the scope of the patent claims.

It is possible for the present disclosure to be used as a myoelectric potential measurement device, and particularly as a myoelectric potential measurement device, a gesture input device, or a user interface device or the like that is able to recognize a movement of an arm with a myoelectric potential being appropriately measured even when not all of a plurality of electrodes are in close contact with the arm.

What is claimed is:

1. A myoelectric potential measurement method comprising:
   (a) by using a bracelet having a plurality of electrodes that come into contact with the arm of the user, measuring a myoelectric potential at each of the plurality of electrodes;
   (b) detecting an orientation of the bracelet when the myoelectric potential is being measured;
   (c) specifying at least one preferred electrode, vertically under which a portion of the arm of the user is positioned, from the plurality of electrodes in accordance with the orientation of the bracelet, and weighting the myoelectric potential measured by the at least one specified preferred electrode, with respect to the each myoelectric potential measured by electrodes other than the at least one preferred electrode from the plurality of electrodes; and
   (d) by using the weighted myoelectric potential, recognizing the movement of the arm of the user, and outputting a recognition result,
   wherein at least one of the (a) to (d) is performed by a processor.

2. The myoelectric potential measurement method according to claim 1,
   wherein, in the (a), the each myoelectric potentials is measured in a time-sequential manner for each of the plurality of electrodes, and,
   in the (d), reference is made to a recognition model that includes a plurality of types of movements of the arm and time-sequential changes in the myoelectric potentials associated with each of the types of movements, to recognize a movement of the arm of the user that corresponds to the time-sequential changes in the each measured myoelectric potential.

3. The myoelectric potential measurement method according to claim 2,
   wherein the plurality of types of movements of the arm includes a movement of a hand of the user.

4. The myoelectric potential measurement method according to claim 1,
   wherein, in the (b), a direction of gravity is detected, and the orientation of the bracelet is an orientation with respect to the direction of gravity.

5. The myoelectric potential measurement method according to claim 4,
   wherein the bracelet is provided with a display unit that shows the recognition result obtained in the (d), and,
   in the (b), the orientation of the bracelet is an orientation of the display unit with respect to the direction of gravity.

6. The myoelectric potential measurement method according to claim 2,
   wherein, in the (d), one recognition model is selected from a plurality of different recognition models in accordance with the measurement state detected in the (b), and,
   in the (d), the selected recognition model is used to recognize the movement of the arm.

7. The myoelectric potential measurement method according to claim 6,
   wherein the plurality of recognition models include a first recognition model indicating a myoelectric potential change pattern for a movement of the arm with which an anterior-side myoelectric potential is likely to occur, and a second recognition model indicating a myoelectric potential change pattern for a movement of the arm with which a posterior-side myoelectric potential is likely to occur.

8. The myoelectric potential measurement method according to claim 1, further comprising:
   (e) storing changes of the orientation of the bracelet that occur over time detected in the (b),
   wherein, in the (d), it is determined whether or not a position of a wrist included in the arm is within a predetermined space of a body of the user, in accordance with the stored changes of the orientation of the bracelet, and the movement of the arm of the user is recognized by the (d) after it is determined that the position of the wrist is within the predetermined space.

9. The myoelectric potential measurement method according to claim 8,
   wherein the predetermined space is a space that is set in a position higher than an elbow of the arm.

10. The myoelectric potential measurement method according to claim 8,
    wherein, in the (d), it is determined whether or not the position of the wrist is within the predetermined space when the position of the wrist included in the arm has moved in a gravitational direction and has entered the predetermined space, in accordance with the stored changes of the orientation of the bracelet, and the movement of the arm of the user is recognized by the (d) after it is determined that the position of the wrist is within the predetermined space when the position of the wrist included in the arm has moved in a gravitational direction and has entered the predetermined space.

* * * * *